United States Patent [19]

Uchida et al.

[11] Patent Number: 4,880,815
[45] Date of Patent: Nov. 14, 1989

[54] IMIDAZOPYRIDYL-ALKYLTHIO-PYRIDINES AND ANTI-PEPTIC ULCER COMPOSITIONS CONTAINING THE SAME

[75] Inventors: Minoru Uchida, Komatsushima; Seiji Morita, Tokushima; Masatoshi Chihiro, Naruto; Kazuyuki Nakagawa, Tokushima, all of Japan

[73] Assignee: Otsuka Pharmaceutical Co., Ltd., Tokyo, Japan

[21] Appl. No.: 109,207

[22] Filed: Oct. 16, 1987

Related U.S. Application Data

[60] Division of Ser. No. 62,429, Jun. 16, 1987, Pat. No. 4,738,970, which is a continuation of Ser. No. 809,881, Dec. 17, 1985, abandoned.

[30] Foreign Application Priority Data

Dec. 18, 1984 [JP] Japan ................................. 59-26706
Dec. 21, 1984 [JP] Japan ................................ 59-271433
Jul. 2, 1985 [JP] Japan ................................ 60-145654
Jul. 12, 1985 [JP] Japan ................................ 60-154708
Nov. 11, 1985 [JP] Japan ................................ 60-252489

[51] Int. Cl.$^4$ .................. A61K 31/435; C07D 471/04
[52] U.S. Cl. ..................................... 514/303; 546/118

[58] Field of Search ................ 546/118, 271; 514/303, 514/339

[56] References Cited

U.S. PATENT DOCUMENTS

| | | | |
|---|---|---|---|
| 3,819,640 | 6/1974 | von Bebenburg | 546/118 |
| 4,045,563 | 8/1977 | Berntsson | 514/338 |
| 4,045,564 | 8/1977 | Berntsson | 514/338 |
| 4,359,465 | 11/1982 | Ruwart | 514/338 |

FOREIGN PATENT DOCUMENTS

| | | | |
|---|---|---|---|
| 254588 | 1/1988 | European Pat. Off. | 546/118 |
| 62-145084 | 6/1987 | Japan | 546/118 |
| 1234058 | 6/1971 | United Kingdom | 546/118 |

*Primary Examiner*—Donald G. Daus
*Attorney, Agent, or Firm*—Finnegan, Henderson, Farabow, Garrett & Dunner

[57] ABSTRACT

Novel tetrahydroquinoline derivatives and salts thereof and novel imidazopyridine derivatives and salts thereof, both having excellent anti-peptic ulcer activities, and are useful as treating agents for peptic ulcers such as gastric ulcer, duodenum ulcer and the like.

13 Claims, No Drawings

IMIDAZOPYRIDYL-ALKYLTHIO-PYRIDINES AND ANTI-PEPTIC ULCER COMPOSITIONS CONTAINING THE SAME

This is a division of application Ser. No. 062,429, filed June 16, 1987, now U.S. Pat. No. 4,738,970, which is a a continuation of application Ser. No. 809,881 filed Dec. 17, 1985 now abandoned.

FIELD OF THE INVENTION

The present invention relates to novel tetrahydroquinoline derivatives and salts thereof, and to novel imidazopyridine derivatives and salts thereof, both having excellent anti-peptic ulcer activities. More particularly, the present invention relates to novel tetrahydroquinoline derivatives and salts thereof, and to novel imidazopyridine derivatives and salts thereof, process for preparing the same and anti-peptic ulcer compositions containing the same as the active ingredient.

The novel tetrahydroquinoline derivatives and salts thereof according to the present invention are represented by the general formula (1),

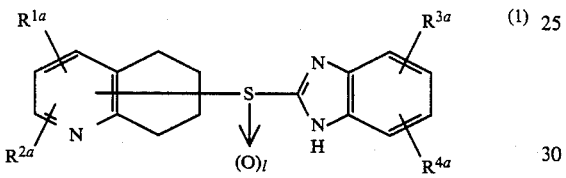

[wherein $R^{1a}$ and $R^{2a}$ are the same or different from each other, and are each a hydrogen atom, a halogen atom, a hydroxy group, a lower alkyl group, a lower alkoxy group, a lower alkenyloxy group, a lower alkynyloxy group or a lower alkoxy-lower alkoxy group; $R^{3a}$ and $R^{4a}$ are the same or different from each other, and are each a hydrogen atom, a halogen atom, a nitro group, a lower alkyl group which may have halogen atoms as the substituents, a lower alkoxy group or a lower alkanoyl group, and l is 0 or 1; as well as the substituted position of a group of the formula

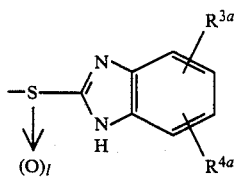

may be of 2- to 8-position in the tetrahydroquinoline skeleton], in addition to the above, novel imidazopyridine derivatives and salts thereof according to the present invention are represented by the general formula (20),

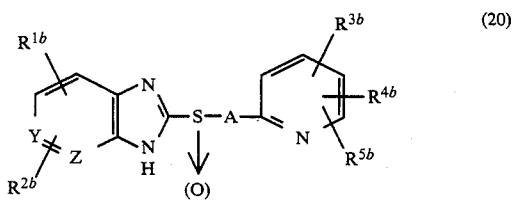

[wherein any one of Z or Y is a group of the formula —CH=, then the other is a nitrogen atom =N—; $R^{1b}$ and $R^{2b}$ are the same or different from each other and are each a hydrogen atom, a lower alkoxycarbonyl group, a halogen atom, a lower alkyl group, an amino group or a hydroxy group; $R^{3b}$, $R^{4b}$ and $R^{5b}$ are the same or different from each other, and are each a hydrogen atom, a lower alkoxy group or a lower alkyl group; A is a lower alkylene group, l is 0 or 1; provided that when Y is a group of the formula =CH—, Z is a nitrogen =N—, and l is 0, then $R^{3b}$, $R^{4b}$ and $R^{5b}$ should not be of hydrogen atoms at the same time].

Novel tetrahydroquinoline derivatives and salts thereof represented by the general formula (1) and novel imidazopyridine derivatives and salts thereof represented by the general formula (20) possess excellent anti-peptic ulcerative activities, and are useful as treating agents for peptic ulcers such as gastric ulcer, duodenum ulcer and the like.

PRIOR ART

Production rate of hydrochloric acid contained in gastric juice secreted from the gastric mucosa is controlled by various physiological factors, among of which biochemical mechanisms relating to the production rate of hydrogen ion ($H^+$) affect eventually as the rate-limiting factors thereto.

In the recent years, there have been found the facts that an adenosine triphosphatase (ATPase) having the property by which the ATPase is activated with hydrogen ion ($H^+$) and potassium ion ($K^+$) in the stomach wall cells controls the production rate of hydrochloric acid. Said ATPase is an enzyme exists specifically in the stomach wall cells, and plays an important role as the key enzyme in the mechanism so called "proton pump". Therefore, an inhibiting agent which can affect the activity of this ATPase can be of a useful agent for inhibiting the secretion of hydrochloric acid produced in the stomach.

Tetrahydroquinoline derivatives and salts thereof represented by the general formula (1) and imidazopyridine derivatives and salts thereof represented by the general formula (20) of the present invention possess specifically both activity for inhibiting the secretion of hydrochloric acid, and for protecting the stomach wall cells, thus the tetrahydroquinoline derivatives and salts thereof, as well as the imidazopyridine derivatives and salts thereof of the present invention inhibit the peptic ulcerative factors from both sides, i.e., inhibiting the attacking factor and protecting factor as well. Furthermore, the tetrahydroquinoline derivatives and salts thereof, as well as imidazopyridine derivatives and salts thereof the present invention have advantageous features, i.e., they only show lower toxicity, while they keep prolonged action for inhibiting the secretion of hydrochloric acid in the stomach.

There have been known some compounds having chemical structural formulas similar to those of tetrahydroquinoline derivatives represented by the general formula (1) in some literatures, e.g., British Pat. Nos. 1,234,058; 1,500,043; U.S. Pat. Nos. 4,045,563; 4,359,465; 3,808,005; and German patent application (Laid-open) No. 2,164,661. Furthermore, there have been known some compounds having chemical structural formulas similar to those of imidazopyridine derivatives represented by the general formula (20) in some literatures, e.g., European patent application No. 0130729 [corresponding to Japanese patent application Kokai (Laid-open) No. 60-36483 (1985)].

Among of these literatures, for example, in British Pat. No. 1,234,058 teaches pyridylalkyloxy and pyridylalkylthioazole derivatives represented by the general formula,

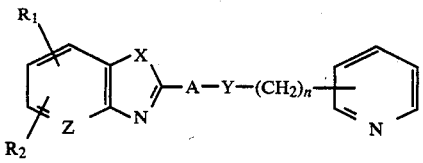

(wherein A is $C_{1-5}$-alkylene or valency bond; X is NH, O or S, Y is S or O; Z is CH or N; $R_1$ is H or $CH_3$; $R_2$ is H or Cl, $NO_2$, or $CH_3$; n is an integer of 1-3), said derivatives show anti-tuberculosis activity, insecticidal activity, anti-fungal activity, anti-viral activity, anthelminthic activity and anti-inflammatory activity.

The above-mentioned pyridylalkoxy and pyridylalkylthioazole derivatives in this literature indeed contain imidazopyridine derivatives similar to those disclosed in the present invention, however apart from the latter derivatives of the present invention, the former derivatives only show quite weak anti-peptic ulcerative activity as shown in the pharmacological test result mentioned later in the present specification.

SUMMARY OF THE INVENTION

An object of the present invention is to provide novel tetrahydroquinoline derivatives and salts represented by the general formula (1), as well as novel imidazopyridine derivatives and salts thereof represented by the general formula (20).

Another object of the present invention is to provide processes for preparing the tetrahydroquinoline derivatives and salts thereof, and for preparing imidazopyridin derivatives and salts thereof.

Further object of the present invention is to provide pharmaceutical composition for treating peptic ulcer containing the above-mentioned tetrahydroquinoline derivatives or salt thereof, or containing the above-mentioned imidazopyridine derivatives or salt thereof as the active ingredient.

DETAILED EXPLANATION OF THE INVENTION

In the present specification, as to the lower alkyl group, a straight chain or branched chain alkyl group having 1 to 6 carbon atoms, such as methyl, ethyl, propyl, isopropyl, butyl, isobutyl, pentyl, hexyl groups can be exemplified.

As to the lower alkoxy group, a straight chain or branched chain alkoxy group having 1 to 6 carbon atoms, such as methoxy, ethoxy, propoxy, isopropoxy, butoxy, isobutoxy, pentyloxy and hexyloxy groups can be exemplified.

As to the halogen atom, there can be exemplified fluorine, chlorine, bromine and iodine atom.

As to the lower alkyl group which may have halogen atoms as the substituents, in addition to the above-mentioned alkyl groups, alkyl group having 1 to 6 carbon atoms which may have 1 to 3 halogen atoms as the substituents, such as trifluoromethyl, 2,2-difluoroethyl, 1,1-dichloroethyl, dichloromethyl, trichloromethyl, tribromomethyl, 2,2,2-trifluoroethyl, 2,2,2-trichloroethyl, 2-chloroethyl, 1,2-dichloroethyl, 3,3,3-trichloropropyl, 3-fluoropropyl, 4-chlorobutyl and 3-chloro-2-methylpropyl groups can be exemplified.

As to the lower alkanoyl group, a straight chain or branched chain alkanoyl group having 1 to 6 carbon atoms such as formyl, acetyl, propionyl, butyryl, isobutyryl, pentanoyl and hexanoyl groups can be exemplified.

As to the lower alkenyloxy group, a straight chain or branched chain alkenyloxy group having 2 to 6 carbon atoms, such as vinyloxy, allyloxy, 2-butenyloxy, 3-butenyloxy, 1-methylallyloxy, 2-pentenyloxy and 2-hexenyloxy groups can be exemplified.

As to the alkynyloxy group, a straight chain or branched chain alkenyloxy group having 2 to 6 carbon atoms, such as ethynyloxy, 2-propynyloxy, 2-butynyloxy, 3-butynyloxy, 1-methyl-2-propynyloxy, 2-pentynyloxy and 2-hexynyloxy groups can be exemplified.

As to the lower alkoxy-lower alkoxy group, a straight chain or branched chain alkyl group having 1 to 6 carbon atoms, having as the substituent a straight chain or branched chain alkyl group having 1 to 6 carbon atoms, such as methoxymethoxy, ethoxymethoxy, propoxymethoxy, butoxymethoxy, pentyloxymethoxy, hexyloxymethoxy, 2-methoxyethoxy, 1-methoxyethoxy, 2-propoxyethoxy, 2-hexyloxyethoxy, 3-methoxypropoxy, 1-methoxypropoxy, 3-butoxypropoxy, 3-pentyloxypropoxy, 4-methoxybutoxy, 3-propoxybutoxy, 4-hexyloxybutoxy, 5-ethoxypentyloxy, 3-propoxypentyloxy, 6-methoxyhexyloxy, 2-ethoxyhexyloxy and 3-pentyloxyhexyloxy groups can be exemplified.

As to the lower alkylene group, a straight chain or branched chain alkylene group having 1 to 6 carbon atoms, such as methylene, ethylene, trimethylene, methylmethylene, ethylmethylene, 2-methyltrimethylene, 2,2-dimethyltrimethylene, 1-methyltrimethylene, tetramethylene, pentamethylene and hexamethylene.

As to the lower alkoxycarbonyl group, an alkoxylcarbonyl group in which the alkoxy moietyl having 1 to 6 carbon atoms, such as methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl group can be exemplified.

The tetrahydroquinoline derivatives and salts thereof represented by the general formula (1) can be prepared by various methods, for example they are prepared by the following reaction formulas.

Reaction formula - 1

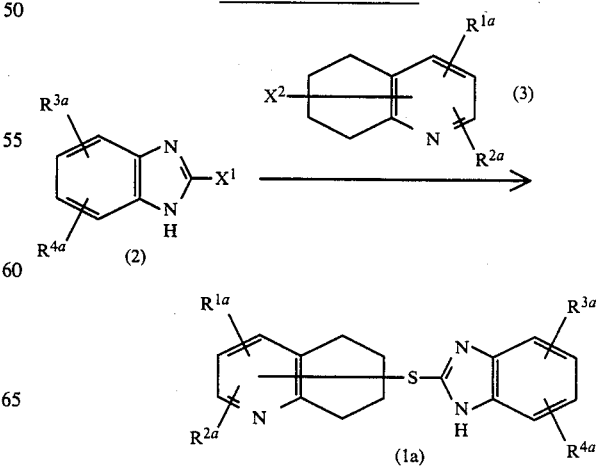

[wherein $R^{1a}$, $R^{2a}$, $R^{3a}$ and $R^{4a}$ are the same as defined above; $X^1$ and $X^2$ are each a mercapto group, a halogen atom, a lower alkanesulfonyloxy group, an arylsulfonyloxy group, or an aralkylsulfonyloxy group; provided that when $X^1$ is a mercapto group, then $X^2$ is a halogen atom, a lower alkanesulfonyloxy group, an arylsulfonyloxy group, or an aralkylsulfonyloxy group; while when $X^2$ is a mercapto group, then $X^1$ is a halogen atom, a lower alkanesulfonyloxy group, an arylsulfonyloxy group, or an aralkylsulfonyloxy group].

In the general formulas (2) and (3), $X^1$ and/or $X^2$ are halogen atoms as defined above; as to the lower alkanesulfonyloxy group, there can be specifically exemplified such as methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy groups; as to the arylsulfonyloxy group, there can be specifically exemplified such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, and α-naphthylsulfonyloxy groups; as to the aralkylsulphonyloxy group, there can be exemplified such as a substituted- or unsubstituted aralkylsulfonyloxy group for example benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 4-methoxybenzylsulfonyloxy, 3-chlorobenzylsulfonyloxy and α-naphthylmethylsulfonyloxy groups.

The reaction of a compound of the general formula (2) with a compound of the general formula (3) can be carried out in a suitable solvent in the presence of a basic compound. As to the solvent used in the reaction, any solvent which may not give any adverse effect can be used, such as water; an alcohol for examples methanol, ethanol or isopropanol; an aromatic hydrocarbon for example benzene, toluene or xylene; an ether for example diethyl ether, tetrahydrofuran, dioxane, monoglyme or diglyme; a ketone for example acetone; an ester methyl acetate or ethyl acetate; a polar solvent for example N,N-dimethylformamide, dimethyl sulfoxide or hexamethylphosphoric triamide; or a mixed solvent thereof. As to the basic compound used in the reaction, an inorganic base for example sodium hydride, sodium hydroxide, potassium hydroxide, sodium carbonate, potassium carbonate, sodium hydrogen carbonate, potassium hydrogen carbonate or silver carbonate; an alkali metal for example metallic sodium or metallic potassium; an alcoholate for example sodium methylate, or sodium ethylate, an organic base for example triethylamine, pyridine, N,N-dimethylaminopyridine, N-methylmorpholine, 1,5-diazabicyclo[4.3.0]nonene-5 (DBN), 1,8-diazabicyclo[5.4.0]undecene-7 (DBU) or 1,4-diazabicyclo[2.2.2]octane (DABCO).

The reaction is carried out, generally at 0°–150° C., preferably at about 0°–100° C., for 1–10 hours. The amount of a compound of the general formula (2) used to a compound of the general formula (3) may be of generally at least an equimolar quantity, preferably an equimolar quantity to 2 times the molar quantity.

Reaction formula - 2

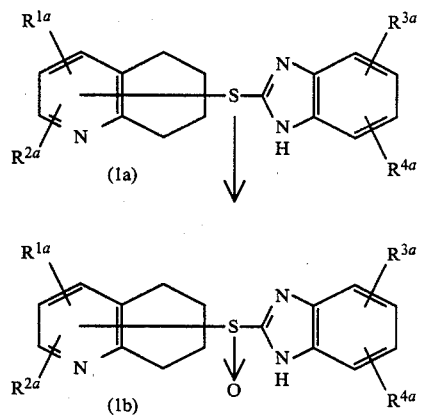

[wherein $R^{1a}$, $R^{2a}$, $R^{3a}$ and $R^{4a}$ are the same as defined above].

The oxidation of a compound of the general formula (1a) is carried out in a suitable solvent, in the presence of an oxidizing agent. As to the solvent used in the oxidation, any solvent which may not give any adverse effect can be used, for examples, water; an organic acid such as formic acid, acetic acid or trifluoroacetic acid; an alcohol such as methanol, ethanol or isopropanol; a halogenated hydrocarbon such as chloroform, dichloromethane or dichloroethane. As to the oxidizing agent used in the oxidation, any oxidizing agent used for oxidizing a sulfide group to a sulfoxide group can be used, such as a peracid for example performic acid, peracetic acid, trifluoroperacetic acid, perbenzoic acid, m-chloroperacetic acid or o-carboxyperacetic acid; hydrogen peroxide; chromic acid, a chromate for example sodium chromate or potassium chromate; permanganic acid, a permanganate for example sodium permanganate or potassium permanganate; an iodate for example sodium metaiodate; a selen compound for example selenium dioxide can be exemplified. The ratio of the amount of oxidizing agent to the amount of compound of the general formula (1a) may be at least an equimolar quantity, preferably an equimolar to 1.5 times the molar quantity of the former to the latter. The oxidation reaction is carried out, generally at −70° to 40° C., preferably at −70° C. to about room temperature, and is completed about 5 minutes to 3 hours.

Reaction formula - 3

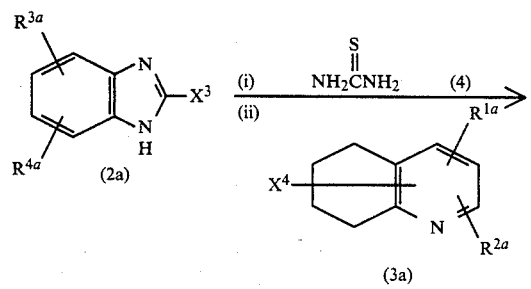

-continued
Reaction formula - 3

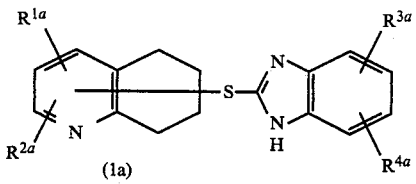

(1a)

[wherein $R^{1a}$, $R^{2a}$, $R^{3a}$ and $R^{4a}$ are the same as defined above; and $X^3$ and $X^4$ are each halogen atoms].

In the above, the reaction (i) of a compound of the general formula (2a) with thiourea (4) is carried out in the presence of a solvent or without solvent. As to the solvent used in the reaction, an alcohol such as methanol, ethanol or propanol; an ether such as diethyl ether, tetrahydrofuran, dioxane or ethylene glycol monomethyl ether; an aromatic hydrocarbon such as benzene, toluene or xylene; a ketone such as acetone or methyl ethyl ketone; or polar solvent such as dimethylformamide, dimethyl sulfoxide or hexamethylphosphoric triamide (HMPA) can be exemplified. The amount of thiourea (4) used in the reaction may be of, generally at least an equimolar quantity, preferably an equimolar to 2 times the molar quantity to a compound of the general formula (2a). The reaction is carried out, generally at room temperature to 200° C., preferably at room temperature to at about 150° C., and is completed for about 1 to 5 hours.

The reaction (ii) of the intermediate product obtained in the reaction (i) with a compound of the general formula (3a) is generally carried out in the presence of a condensing agent. As to the condensing agent used in the reaction (ii), a basic compound is generally used. As to the basic compound, any known basic compound can be used, for example, an inorganic basic compound, such as sodium hydroxide, potassium hydroxide, sodium carbonate, potassium carbonate, sodium hydrogen carbonate, potassium hydrogen carbonate or silver carbonate; an alkali metal such as metallic sodium or metallic potassium; an alcoholate such as sodium methylate or sodium ethylate; an organic basic compound such as triethylamine, pyridine, N,N-dimethylaniline, N-methylmorpholine, 4-dimethylaminopyridine, DBN, DBU or DABCO can be exemplified.

Said reaction is carried out without solvent or in the presence of a solvent. As to the solvent, any inert solvent which may not give any adverse effect can be used, for example water, an alcohol such as methanol, ethanol, propanol, butanol or ethylene glycol; an ether such as diethyl ether, tetrahydrofuran, dioxane, monoglyme or diglyme; a ketone such as acetone or methyl ethyl ketone; an aromatic hydrocarbon such as benzene, toluene or xylene; an ester such as methyl acetate or ethyl acetate; an aprotic polar solvent such as dimethylformamide, dimethyl sulfoxide or hexamethylphosphoric triamide; or a mixed solvent thereof can be used.

Furthermore, said reaction is advantageously carried out in the presence of a metal iodide such as sodium iodide or potassium iodide. The ration of the amount of compound (2a) to the amount of compound (3a) is not specifically restricted, and can be selected from a wide range, and generally 0.5 to 5.0 times the molar quantity, preferably 0.5 to 2 times the molar quantity of the latter can be used to the former. The reaction temperature is not restricted specifically, and generally the reaction is carried out at $-30°$ to 200° C., preferably at 0° to 160° C., and is completed, generally in 1 to 30 hours.

Reaction formula - 4

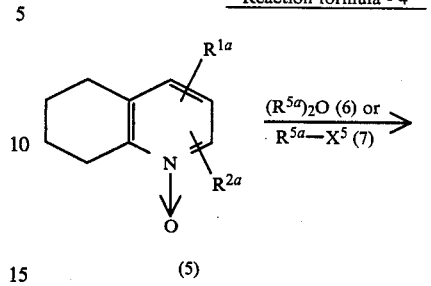

(5)

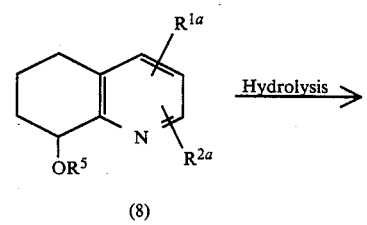

(8)

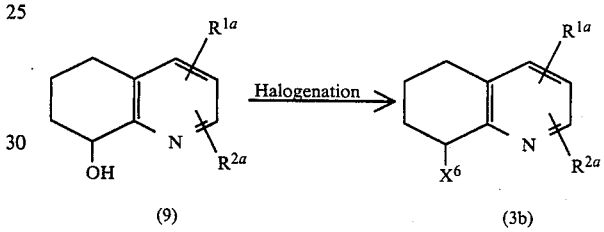

(9)            (3b)

[wherein $R^{1a}$ and $R^{2a}$ are the same as defined above; $R^{5a}$ is a lower alkanoyl group; $X^5$ and $X^6$ are each a halogen atom.]

The reaction of a compound of general formula (5) with a compound of the general formula (6) or (7) is carried out in suitable solvent or without solvent. As to the solvent used in the reaction, any solvent which may not give any adverse effect to the reaction can be used, for example a halogenated hydrocarbon such as dichloromethane, dichloroethane, chloroform or carbon tetrachloride; an aromatic hydrocarbon such as benzene, toluene or xylene; an ether such as diethyl ether, tetrahydrofuran or dioxane; or pyridine can be used. The ratio of the amount of a compound of the general formula (6) or (7) to the amount of a compound of the general formula (5) is at least an equimolar quantity, preferably a large excess quantity of the former may be used to the latter. The reaction is carried out generally at 0° to 150° C., preferably at 0° C. to about 100° C., and is completed in 1 to 5 hours.

The hydrolysis reaction of a compound of the general formula (8) is carried out in the presence of a hydrolysis catalyst for example, an inorganic acid such as hydrohalic acid for example hydrochloric acid or hydrobromic acid, sulfuric acid or phosphoric acid; an alkali metal compound for example an alkali metal hydroxide such as sodium hydroxide or potassium hydroxide, an alkali metal carbonate or hydrogen carbonate such as sodium carbonate, potassium carbonate, or sodium hydrogen carbonate, in a suitable solvent or without solvent (for example water, an alcohol such as methanol, ethanol or a mixed solvent thereof), at room temperature to 150° C., preferably at 50° to 100° C., for 30 minutes to 24 hours.

The halogenation of a compound of the general formula (9) is carried out in the presence or absence of a solvent by using a usual halogenating agent. As to the halogenating agent, any known halogenating agent selected from a wide range may be used, for example a halogen molecule such as bromine or chlorine; a hydrohalic acid such as hydrobromic acid, hydrochloric acid; thionyl chloride; a phosphorus halide such as phosphorus pentachloride, phosphorus tribromide or phosphorus oxychloride can be used. The ratio of the amount of halogenating agent used is at least an equimolar quantity, preferably an equimolar to a large excess quantity thereof may be used to a compound of the general formula (9). As to the solvent used in the halogenation, there may be exemplified a halogenated hydrocarbon such as dichloromethane, dichloroethane, chloroform or carbon tetrachloride; acetic acid; propionic acid, sulfuric acid or water. The halogenation is carried out generally at 0°–150° C., preferably at 0°–100° C., and is completed in 1 to 24 hours.

On the other hand, a compound of the general formula (3b) can be prepared directly by reacting a compound of the general formula (5) with a halogenating agent in the presence or absence of a suitable solvent. As to the solvent used in this halogenation, the solvent used in the halogenation of a compound of the general formula (9) may be exemplified. As to the halogenating agent, there can be exemplified an alkane- or arylsulfonylhalide such as methanesulfonyl chloride, p-toluenesulfonyl chloride or benzenesulfonyl chloride. The amount of halogenating agent used may be at least an equimolar quantity, preferably an equimolar to 2 times the molar quantity to a compound of the general formula (5). The said halogenation is carried out at generally at 0°–150° C., preferably at 0°–100° C., and is completed in 1 to 10 hours.

Reaction formula - 5

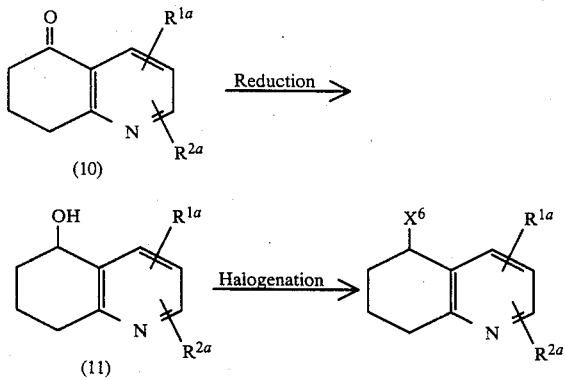

[wherein $R^{1a}$, $R^{2a}$ and $X^6$ are the same as defined above].

The reduction of a compound of the general formula (10) is carried out by using a usual hydrogenating agent. As to the hydrogenating agent, sodium borohydride, lithium aluminum hydride or dialkylaluminum hydride such as diisobutylaluminum hydride (DIBAL) or diborane can be exemplified. The amount of the hydrogenating agent is generally 0.1-3 times the molar quantity, preferably 0.5-2 times the molar quantity to a compound of the general formula (10). This reduction is carried out, generally in a suitable solvent, for example water, a lower alcohol such as methanol, ethanol or isopropanol; an ether such as tetrahydrofuran, diethyl ether or diglyme; an aromatic hydrocarbon such as benzene, toluene or xylene, and at generally −60° to 50° C., preferably at −40° C. to room temperature, and is completed in 10 minutes to 5 hours. When lihium aluminum hydride, dialkylaluminum hydride or diborane is used as the reducing agent, an anhydrous solvent such as diethyl ether, tetrahydrofuran, diglyme, benzene, toluene or xylene may be used. The halogenation of a compound of the general formula (11) is carried out under conditions simular to that employed in the halogenation of a compound of general formula (9).

In the Reaction formula-4, a compound of the general formula (5) used as the starting material contains some novel compounds, and they can be prepared by the following Reaction formula-6 follows.

Reaction formula - 6

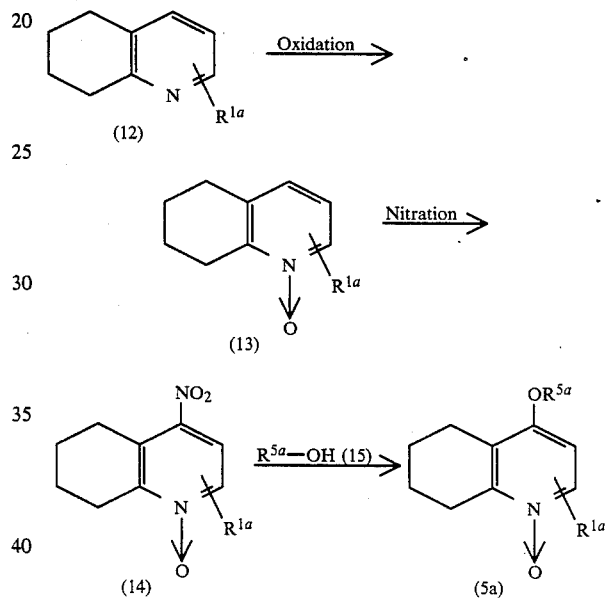

[wherein $R^{1a}$ is the same as defined above; $R^{5a}$ is a lower alkyl group, a lower alkenyl group, a lower alkynyl group or a lower alkoxy-lower alkyl group; provided that $R^{1a}$ is substituted at 2- or 3-position in the tetrahydroquinoline skeleton.]

The oxidation of a compound of the general formula (12) is carried out in a suitable solvent, in the presence of an oxidizing agent. As to the solvent and oxidizing agent used in the oxidation, any solvent and oxidizing agent exemplified in the oxidation of a compound of the general formula (1a) in the above-mentioned reaction formula-2 can be used. The amount of the oxidizing agent may be at least an equimolar quantity, preferably an equimolar to 1.5 times the molar quantity to the compound of the general formula (12). Said oxidation is carried out generally at −20° to 120° C., preferably −20° to about 100° C., and is completed in 5 minutes to 5 hours.

The nitration of a compound of the general formula (13) is carried out under conditions similar to those employed in nitration of common aromatic compounds, for example in the absence or presence of a suitable inert solvent by using a nitrating agent. As to the inert solvent, acetic acid, acetic anhydride, concentrated sulfuric acid or the like can be exemplified. As to the nitrating agent, fuming nitric acid, concentrated nitric acid, mixed acid (a mixed liquid of nitric acid with sulfuric acid, fuming sulfuric acid, phosphoric acid or acetic anhydride) or a mixture of an alkali metal nitrate such as potassium nitrate or sodium nitrate with sulfuric acid can be exemplified. The amount of the above-mentioned nitrating agent may be an equimolar quantity, and generally a large excess quantity to the starting material, the nitration is advantageously carried out at 0° C. to 100° C. for 1 to 6 hours.

The reaction of a compound of the general formula (14) with a compound of the general formula (15) can be carried out in the presence or absence of a suitable solvent, in the presence of a basic compound. As to the solvent used in the reaction, an aromatic hydrocarbon such as benzene, toluene or xylene; an ether such as diethyl ether, tetrahydrofuran, dioxane, monoglyme or diglyme; a ketone such as acetone, an ester such as methyl acetate or ethyl acetate; an aprotic polar solvent such as N,N-dimethylfomamide, dimethyl sulfoxide or hexamethylphosphoric triamide; or a mixture thereof can be exemplified. As to the basic compound used in this reaction, any basic compound exemplified in the above mentioned reaction formula-1 can be used. The amount of a compound of the general formula (15) may be an equimolar quantity, generally a large excess quantity to a compound of the general formula (14), and the reaction is carried out generally at 0° to 150° C., preferably at room temperature to about 100° C. and is completed in 1 to 5 hours.

The imidazopyridine derivatives and salts thereof represented by the general formula (20) can be prepared by various methods, for example they are prepared by the following reaction formulas.

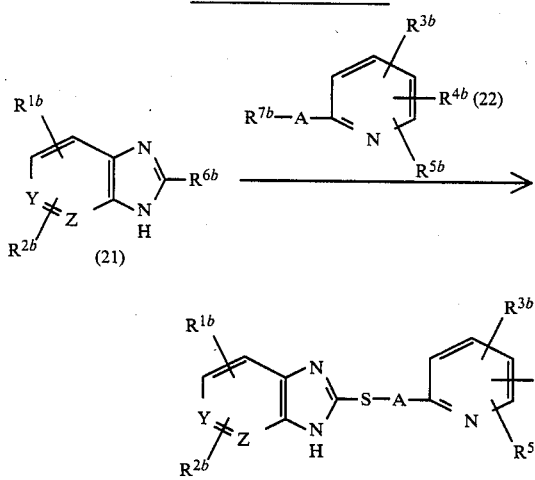

Reaction formula - 7

[wherein $R^{1b}$, $R^{2b}$, $R^{3b}$, $R^{4b}$, $R^{5b}$, Z, Y and A are the same as defined above; and $R^{6b}$ and $R^{7b}$ are each a mercapto group, a halogen atom, a lower alkanesulfonyloxy group, an arylsulfonyloxy group or an aralkylsulfonyloxy group; provided that when $R^{6b}$ is a mercapto group, then $R^{7b}$ is a halogen atom, a lower alkanesulfonyloxy group, an arylsulfonyloxy group or an aralkylsulfonyloxy group; alternatively when $R^{7b}$ is a mercapto group, then $R^{6b}$ is a halogen atom, a lower alkanesulfonyloxy group, an arylsulfonyloxy group or an aralkylsulfonyloxy group].

In the definitions of $R^{6b}$ and/or $R^{7b}$ shown in the general formulas (21) and (22), the halogen atom is the same as defined above; the lower alkanesulfonyloxy group is specifically exemplified such as methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy groups; the arylsulfonyloxy group is specifically exemplified such as substituted- or unsubstituted-arylsulfonyloxy groups for example phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups; the aralkylsulfonyloxy group is specifically exemplified such as substituted- or unsubstituted-aralkylsulfonyloxy groups for example benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy groups.

The reaction of a compound of the general formula (21) with a compound of the general formula (22) can be carried out in a suitable solvent, in the presence of a basic compound. As to the solvent used in the reaction, any inert solvent which does not give any adverse effect to the reaction can be used, for example, water; alcohols such as methanol, ethanol, isopropanol or the like; aromatic hydrocarbons such as benzene, toluene, xylene or the like; ethers such as diethyl ether, tetrahydrofuran, dioxane, monoglyme, diglyme or the like; ketones such as acetone or the like; esters such as methyl acetate, ethyl acetate or the like; polar solvents such as N,N-dimethylformamide, dimethyl sulfoxide or hexamethylphosphoric triamide or the like can be exemplified. As to the basic compound used in the reaction, inorganic bases such as sodium hydride, sodium hydroxide, potassium hydroxide, sodium carbonate, potassium carbonate, sodium hydrogen carbonate, potassium hydrogen carbonate, silver carbonate or the like; alkali metal such as metallic sodium and metallic potassium, alcoholates such as sodium methylate, sodium ethylate or the like; and organic basic compound such as triethylamine, pyridine, N,N-dimethylaminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO) or the like can be exemplified.

The reaction is generally carried out at 0°–150° C., preferably at 0° C. to about 100° C., and is completed in about 1 to 10 hours. The amount of a compound of the general formula (22) to the amount of a compound of the general formula (21) is generally at least an equimolar quantity, preferably an equimolar to 1.5 times the molar quantity may be used.

Reaction formula - 8

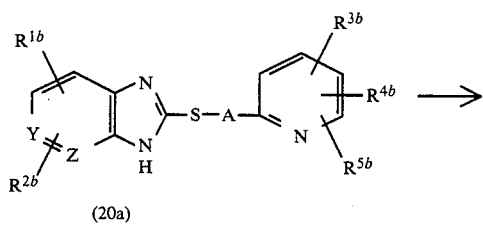

(20a)

-continued
Reaction formula - 8

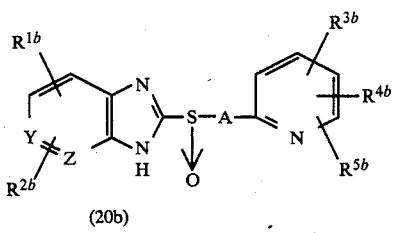

(20b)

[wherein $R^{1b}$, $R^{2b}$, $R^{3b}$, $R^{4b}$, $R^{5b}$, A, Z and Y are the same as defined above].

The oxidation of a compound of the general formula (20a) is carried out in a suitable solvent, in the presence of an oxidizing agent. As to the solvent used in the oxidation, any inert solvent which does not give any adverse effect to the oxidation can be used, for example, water; organic acids such as formic acid, acetic acid, trifluoroacetic acid and the like; alcohols such as methanol, ethanol and the like; halogenated hydrocarbons such as chloroform, dichloromethane and the like can be exemplified. As to the oxidizing agent, any oxidizing agent which can be able to oxidize sulfide group can be used, for example, peracids such performic acid, peracetic acid, trifluoroperacetic acid, perbenzoic acid, m-chloroperbenzoic acid, o-carboxyperbenzoic acid or the like; hydrogen peroxide; chromic acid, chromates such as sodium chromate and potassium chromate or the like; permanganic acid; permangantes such as sodium permanganate and potassium permangante and the like can be exemplified.

The amount of the oxidizing agent to be used to a compound of the general formula (20a) is at least an equimolar quantity, preferably an equimolar to 1.5 times the molar quantity may be used. The oxidation is generally carried out at $-20°$ to $40°$ C., preferably at $-20°$ C. to about room temperature, and is completed in 5 minutes to 3 hours.

Reaction formula - 9

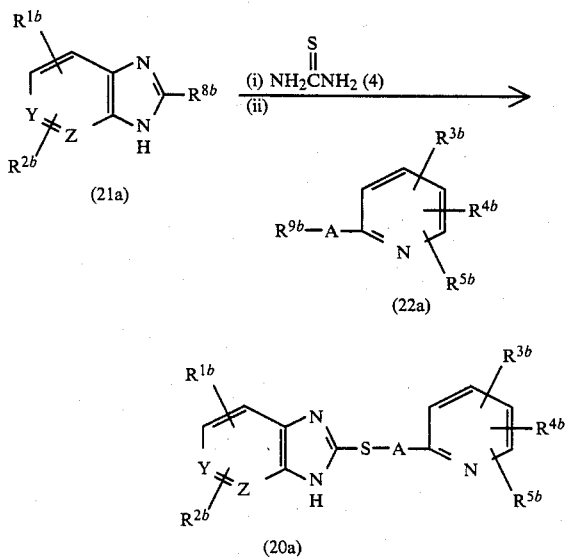

[wherein $R^{1b}$, $R^{2b}$, $R^{3b}$, $R^{4b}$, $R^{5b}$, A, Z, and Y are the same as defined above; $R^{8b}$ and $R^{9b}$ are each a halogen atom].

The reaction (i) of a compound of the general formula (21a) with thiourea (4) is carried out in the presence or absence of a solvent. As to the solvent used in this reaction, alcohols such as methanol, ethanol, propanol and the like; ethers such as diethyl ether, tetrahydrofuran, dioxane, ethylene glycol monomethyl ether or the like; aromatic hydrocarbons such as benzene, toluene, xylene and the like; ketones such as acetone, methyl ethyl ketone and the like; polar solvents such as dimethylformamide, dimethyl sulfoxide, hexamethylphosphoric triamide (HMPA) and the like can be exemplified. The amount of thiourea (4) to be used to a compound of the general formula (21a) is generally at least an equimolar quantity, preferably an equimolar to 2 times the molar quantity may be used to a compound of the general formula (21a). The reaction is generally carried out at room temperature to $200°$ C., preferably at room temperature to about $150°$ C., and is completed in 1-5 hours.

The reaction (ii) of the intermediate product with a compound of the general formula (22a) is generally carried out in the presence of a condensing agent. As to the condensing agent, generally basic compound is used. As to the basic compounds, inorganic bases such as sodium hydroxide, potassium hydroxide, sodium carbonate, potassium carbonate, sodium hydrogen carbonate, potassium hydrogen carbonate silver carbonate and the like; alkali metals such as metallic sodium metallic potassium and the like; alcoholates such as sodium methylate, sodium ethylate and the like; organic basic compounds such as triethylamine, pyridine, N,N-dimethylaniline, N-methylmorpholine, 4-dimethylaminopyridine, DBN, DBU, DABCO and the like can be exemplified.

This reaction is carried out in the absence or presence of a solvent. As to the solvent, any inert solvent which does not give any adverse effect to the reaction may be used, for example, water, alcohols such as methanol, ethanol, propanol, butanol, ethylene glycol and the like; ethers such as diethyl ether, THF, dioxane, monoglyme, diglyme and the like; ketones such as acetone, methyl ethyl ketone and the like; aromatic hydrocarbons such as benzene, toluene, xylene and the like; esters such as methyl acetate, ethyl acetate; aprotic polar solvents such as DMF, DMSO, HMPA and the like can be exemplified.

This reaction can advantageously be carried out in the presence of a metal iodide such as sodium iodide, potassium iodide and the like. The ratio of the amount of a compound of the general formula (21a) to the amount of a compound of the general formula (22a) is not specifically restricted, and can be selected from a wide range, generally the latter is used in 0.5 molar quantity to 5 times quantity, preferably 0.5 to 2 times the molar quantity of the latter is used to the former. The reaction temperature is not specifically restricted, and generally the reaction is carried out at $-30°$ to $200°$ C., preferably $0°$ to $160°$ C., and is generally completed in about 1 to 30 hours.

Compounds of the general formula (21) partially contain novel compounds, and they can be prepared by the following reaction formula-10.

Reaction formula - 10

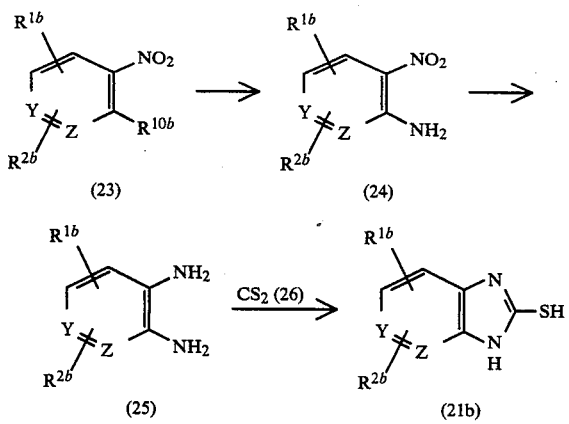

[wherein $R^{1b}$, $R^{2b}$, Z and Y are the same as defined above; and $R^{10b}$ is a halogen atom].

The amination of a compound of the general formula (23) is carried out in a suitable solvent by reacting it with an amination agent. As to the solvent used in the amination can be exemplified ethers such as diethyl ether, tetrahydrofuran, dioxane and the like; aromatic hydrocarbons such as benzene, toluene, xylene and the like; alcohols such as methanol, ethanol, isopropanol and the like; polar solvents such as dimethylformamide, dimethyl sulfoxide, HMPA and the like.

As to the amination agent used in the reaction, ammonia gas, ammonia water, sodium amide and the like can be exemplified. The amount of amination agent used in the reaction may be at least an equimolar quantity, and generally a large excess quantity to compound of the general formula (23). The amination is generally carried out at 0° to 200° C., preferably at room temperature to about 150° C., and is completed in about 5 minutes to 10 hours.

The reduction of a compound of the general formula (24) is carried out for example (i) by catalytically reducing in a suitable solvent with a catalyst, or (ii) by reducing in an inert solvent with a reducing agent such as a mixture of a a metal or metal salt with an acid; a metal or a metal salt with an alkali metal hydroxide, sulfide, ammonium salt or the like.

In carrying out the catalytic reduction (i), as to the solvent used in the reduction, water, acetic acid, alcohols such as methanol, ethanol, isopropanol and the like; hydrocarbons such as hexane, cyclohexane and the like; ethers such as diethylene glycol dimethyl ether, dioxane, THF, diethyl ether and the like; esters such as ethyl acetate, methyl acetate and the like; aprotic polar solvent such as dimethylformamide and the like and mixed solvent thereof can be exemplified. As to the catalysts used in the catalytic reduction, palladium, palladium black, palladium-carbon, platinum, platinum oxide, copper chromite, Raney nickel and the like can be exemplified.

The amount of the catalyst used in the catalytic reduction may be 0.02–1.00 times by weight to compound of the general formula (24). The reduction is generally carried out at −20° to 100° C., preferably at 0° to 70° C., under 1 to 10 atmospheric pressure of hydrogen pressure, and is completed generally in 0.5 to 10 hours.

In carrying out of the reduction (ii), a mixture of iron, zinc, tin or stannous chloride with a mineral acid such as hydrochloric acid or sulfuric acid; iron, ferrous sulfate; ainc or tin; a mixture of tin with an alkali metal hydroxide such as sodium hydroxide, sulfide such as ammonium sulfide, ammonia water, ammonia salt such as ammonium chloride can be used as the reducing agent. As to the inert solvent used in the reduction, water, acetic acid, methanol, ethanol, dioxane and the like can be exemplified. The reaction conditions of the above-mentioned reduction may be suitably selected depend on the reducing agent being employed, and the reaction is generally carried out at −50° to 100° C., and is completed in about 0.5 to 10 hours. For example, in the case of using stannous chloride with hydrochloric acid is used as the reducing agent, the reaction may be carried out advantageously at −20° to 70° C. The amount of the reducing agent may be at least an equimolar quantity, preferably an equimolar to 3 times the molar quantity may be used to the starting material to be reduced.

The reaction of a compound of the general formula (25) with a compound of the general formula (26) is carried out in a suitable solvent. As to the solvent, alcohols such as methanol, ethanol, isopropanol and the like; aromatic hydrocarbon such as benzene, toluene, xylene and the like; halogenated hydrocarbons such as chloroform, dichloromethane, carbon tetrachloride and the like; ethers such as diethyl ether, tetrahydrofuran, dioxane and the like; polar solvents such as dimethylformamide, dimethyl sulfoxide, hexamethylphosphoric triamide and the like can be exemplified. The reaction is carried out generally at 0° to 100° C., preferably at 0° to about 50° C., and is completed in 1 to about 24 hours.

Among compounds of the general formula (20), a compound wherein at least any one of $R^{1b}$ and $R^{2b}$ is amino group can be introduced to a compound wherein at least any one of $R^{1b}$ and $R^{2b}$ in the general formula (20) is hydroxy group by diazodizing the former compound. Said diazotization can be carried out in a suitable solvent, in the presence of an acid by reacting with a diazotizing agent. As to the solvent used in the diazotization, water, ethers such as dioxane, tetrahydrofuran and the like and mixed solvent thereof can be exemplified. As to the acid used in the diazotization, mineral acids such as hydrochloric acid, hydrobromic acid, sulfuric acid and the like; organic acids such as acetic acid, propionic acid and the like can be exemplified. As to the dizaotizing agent, sodium nitrite, ethyl nitrite, alkyl nitrate such as isoamyl nitrite can be exemplified. The amount of diazotizing agent may be at least an equimolar quantity, preferably 1 to 1.5 times the molar quantity to the starting material. The diazodization is carried out at 0° to about 5° C., and is completed in 5 minutes to 3 hours.

Among the compounds represented by the general formula (1), a compound having at least one halogen atom for the symbol $R^{1a}$ or $R^{4a}$ can be converted into a compound having at least one hydroxy group for the symbol $R^{1a}$ or $R^{4a}$ among the compounds represented by the general formula (1), by dydrolyzing a compound (1) under conditions similar to those employed in the hydrolysis of a compound of the general formula (8) in the reaction formula-4.

Among tetrahydroquinoline derivatives of the general formula (1) and imidazopyridine derivatives of the general formula (20), those having acid groups can be easily converted into their salts by reacting with common pharmaceutically acceptable basic compounds. As to the pharmaceutically acceptable basic compounds, metal hydroxides such as sodium hydroxide, potassium hydroxide, calcium hydroxide and the like, metal carbonates and hydrogen carbonates such as sodium carbonate, sodium hydrogen carbonate and the like; alkali metal alcoholates such as sodium methylate, potassium ethylate and the like can be exemplified. Furthermore, among tetrahydroquinoline derivatives of the general formula (1) and imidazopyridine derivatives of the general formula (20), those having basic groups can easily be converted into their acid-addition salts by reacting with common pharmaceutically acceptable acids. As to the pharmaceutically acceptable acids, inorganic acids such as sulfuric acid, hitric acid, hydrochloric acid, hydrobromic acid and the like; organic acids such as acetic acid, p-toluenesulfonic acid, ethanesulfonic acid, oxalic acid, maleic acid succinic acid, benzoic acid and the like can be exemplified.

Compounds prepared according to the preparent invention including inevitably their optical isomers and stereoisomers.

Compounds prepared by the above-mentioned various reaction formulas according to the present invention can easily be separated and purified from the reaction systems by usual separation means such as distillation, recrystallization, column chromatography, preparative thin-layer chromatography, solvent extraction and the like.

Compounds of the present invention are useful as anti-peptic ulcer agent, and can be used in any form of usual preparations of pharmaceutical compositions together with usual pharmaceutically acceptable carriers. Examples of pharmaceutically acceptable carriers which are selected depending on the desired form of pharmaceutical compositions including diluents and excipients such as fillers, diluents, binders, wetting agents, disinegrating agents, surface active agents, lubricants, and the like. The pharmaceutical compositions can be selected from any desired unit form including tablets, pills, powders, liquors, suspensions, emulsions, granules, capsules, supositories, injection preparations (solutions, suspensions, etc.) and others.

For the purpose of to shape in the form of tablets, carriers which are widely used in this field can be used, for example excipients such as lactose, white sugar, sodium chloride, glucose, urea, starch, calcium carbonate, kaolin, crystalline cellulose, silic acid, etc.; binding agents such as water, ethanol, propanol, simple syrup, glucose solutions, starch solutions, gelatin solutions, carboxymethyl cellulose, shelac, methyl cellulose, calcium phosphate, polyvinyl pyrrolidone, etc.; disintegrating agents such as dried starch, sodium alginate, agar-agar powder, laminalia powder, sodium hydrogen carbonate, calcium carbonate, fatty acid esters of polyoxyethylene sorbita, sodium laurylsulfonate, monoglyceride of stearate, starch, lactose, etc.; desintegration inhibitors such as sucrose, stearin, coconut butter, hydrogenated oils, etc.; absorption accelerators such as quaternary ammonium bases, sodium laurysulfonate, etc.; wetting agents such as glycerin, starch, etc.; adsorbing agents such as starch. lactose, kaolin, bentonite, colloidal silic acid, etc.; and lubricants such as purified talk, stearates, boric acid powder, polyethylene glycols, etc. If necessary, the tablets can further by coated with usual coating materials as to make then into coated tablets, for example tablets coated with sugar, tablets coated with gelatin film, tablets coated with enteric coating layers, tablets coated with films or double layer tablets as well as multiple layer tablets, etc.

For the purpose of to shape in the form of pills, any carrier which is known and used widely in this field can be used, for example, excipients such as glucose, lactose, starch, coconut butter, hydrogenated vegetable oils, kaolin, talc, etc.; binders such as powdered gum arabic, powdered tiagacanth gum, gelatin, ethanol, etc.; desintegrating agents such as laminaria, agar-agar, etc.

For the purpose of to shape in the form of suppositories, carriers which are known and widely used in this field can also be used, for example, polyethylene glycols, coconut butter, higher alcohols, gelatin, semi-synthesized glycerides, etc.

For the purpose of to make in the form of injection preparations, solutions and suspensions prepared are further sterilized and are preferably isotonic to the blood. In preparing the injection preparations in the form of solutions, emulsions, and suspensions, any carrier which is known and is widely used in this field can also be used, for example water, ethanol, propylene glycol, ethoxylated isostearyl alcohol, polyoxylated isostearyl alcohol, polyoxyethylene sorbitan fatty acid esters, etc.; glucose or glycerin may be added to the desired injection preparations of anti-peptic ulcer compositions to make them isotonic.

Furthermore, usual dissolving agents, buffer solutions, analgesic agents may be added. Also coloring materials, preservatives, perfumes, seasoning agents, sweetening agents and other medicines may be added in the desired pharmaceutical preparations, if necessary.

The amount of tetrahydroquinoline derivatives of the general formula (1) and imidazopyridine derivatives of the general formula (20) to be contained in anti-peptic ulcer composition of the present invention is not specifically restricted, and can suitably be selected from a wide range, and generally 1 to 70% by weight, preferably 5 to 50% by weight of said derivatives is contained in the pharmaceutical composition.

Methods for administering the above-mentioned anti-peptic ulcer compositions are not specifically restricted, and the compositions can be used in various forms of preparations depending upon the age, the distinction of sex, the degree of symptoms and other conditions of the patient. For example, tablets, pills, solutions, suspensions, emulsions, granules, and capsules are administered orally; injection preparations are administered intraveneously singly or administered with usual injectable transfusions such as glucose solutions, amino acids solutions, etc.; if necessary, the injection preparations are administered singly intramuscularly, intracutaneously, subcutaneously or intraperitoneally; and the suppositories are administered into rectum.

The dosage of the anti-peptic ulcer composition containing tetrahydroquinoline derivatives and/or imidazolidine derivatives of the present invention can be selected suitably according to the methods for administrations, the age of the patient, the distinction of sex and other conditions as well as the degree of the symptoms, and generally 0.6 to 50 mg of the derivatives per 1 kg of the body weight per day may be administered, and 10 to 1000 mg of the active ingredient may be contained in the administration unit form.

Next, the present invention will be specifically explained by illustrating Examples of pharmaceutical preparations, Reference Examples, Examples and Pharmacological Tests, however the present invention is not restricted only thereto.

| Example of preparation of film coated tablets - 1 | |
| --- | --- |
| 4-Allyloxy-8-(2-benzimidazolyl)sulfinyl-3-methyl-5,6,7,8-tetrahydroquinoline | 150 g |
| Avicel (A trademark for microcrystalline cellulose, manufactured by Asahi Chemical Industry Co., Ltd.) | 40 g |
| Corn starch | 30 g |
| Magnesium stearate | 2 g |
| Hydroxypropyl methyl cellulose | 10 g |
| Polyethylene glycol-6000 | 3 g |
| Castor oil | 40 g |
| Ethanol | 40 g |

4-Allyloxy-8-(2-benzimidazolyl)sulfinyl-3-methyl-5,6,7,8-tetrahydroquinoline, Avicel, corn starch and magnesium stearate were admixed together and ground, then the mixture obtained was shaped into tablets by using a tablet machine (R 10 mm). Then the tablets obtained were coated with a film coating agent consisting of hydroxypropyl methyl cellulose, polyethylene glycol-6000, castor oil and ethanol to prepare film coated tablets having the above-mentioned formulation.

| Example of preparation of film coated tablets - 2 | |
| --- | --- |
| 5-(5-Methoxy-2-benzimidazolyl)sulfinyl-5,6,7,8-tetrahydroquinoline | 150 g |
| Avicel (A trademark for microcrystalline cellulose, manufactured by Asahi Chemical Industry Co., Ltd.) | 40 g |
| Corn starch | 30 g |
| Magnesium stearate | 2 g |
| Hydroxypropyl methyl cellulose | 10 g |
| Polyethylene glycol-6000 | 3 g |
| Castor oil | 40 g |
| Ethanol | 40 g |

By procedures similar to those described in the above-mentioned Example of preparation of film coated tablets-1, there were prepared film coated tablets having the above-mentioned formulation.

| Example of preparation of film coated tablets - 3 | |
| --- | --- |
| 2-[(3,5-Dimethyl-4-methoxy-2-pyridyl)methylthio]imidazo[4,5-b]pyridine | 150 g |
| Avicel (A trademark for microcrystalline cellulose, manufactured by Asahi Chemical Industry Co., Ltd.) | 40 g |
| Corn starch | 30 g |
| Magnesium stearate | 2 g |
| Hydroxypropyl methyl cellulose | 10 g |
| Polyethylene glycol-6000 | 3 g |
| Castor oil | 40 g |
| Ethanol | 40 g |

By procedures similar to those described in the above-mentioned Example of preparation of film coated tablets-1, there were prepared film coated tablets having the above-mentioned formulation.

| Example of preparation of multi-layer tablets - 1 | |
| --- | --- |
| 4-Allyloxy-8-(5,6-dimethyl-2-benzimidazolyl)sulfinyl-3-methyl-5,6,7,8-tetrahydroquinoline | 150.0 g |
| Citric acid | 1.0 g |
| Lactose | 33.5 g |
| Calcium secondary phosphate | 70.0 g |
| Pluronic F-68 (Trademark for a nonionic series of polyoxyalkylene derivative or propylene glycol, manufactured by BASF-Wyandotte Corp.) | 30.0 g |
| Sodium laurylsulfate | 15.0 g |
| Polyvinylpyrrolidone | 15.0 g |
| Polyethylene glycol (Carbowax 1500, manufactured by Union Carbide Corp.) | 4.5 g |
| Polyethylene glycol (Carbowax 6000, manufactured by Union Carbide Corp.) | 45.0 g |
| Corn starch | 30.0 g |
| Dried sodium laurylsulfate | 3.0 g |
| Dried magnesium stearate | 3.0 g |
| Ethanol | q.s. |

4-Allyloxy-8-(5,6-dimethyl-2-benzimidazolyl)sulfinyl-3-methyl-5,6,7,8-tetrahydroquinoline, citric acid, lactose, calcium secondary phosphate, Pluronic F-68 and sodium laurylsulfate were mixed together. The mixture obtained was sieved by No. 60 screen, then the sieved mixture was wet granulated with an alcoholic solution containing polyvinylpyrrolidone, Carbowax 1500 and Carbowax 6000. The granules were made into paste-like semi-solid by adding ethanol, if necessary. Then corn starch was added thereto and the mixture was kneaded continuously until the mixture was formed into granules having uniform granular size. The granules thus obtained were sieved through No. 10 screen, and the sieved granules were placed in a tray and were dried in an oven at 100° C. for 12 to 14 hours. The dried granules were sieved through No. 16 screen, and the sieved granules were admixed with dried sodium laurylsulfate and dried magnesium stearate, then the obtained mixture was shaped into the desired shape by using a tablet machine. The surface of thus obtained tablets (which will become the core portion of the desired multi-layer tablets) were treated with varnish, and the surface of the varnish treated tablets (core portion) were further treated by coating with talcum powder so as to protect the surface of the tablets from the absorption of moisture. The surface of the core portion was coated with under-coating layer, and sufficient number of varnish coating layers were given so as to make the tablets for oral administration. The under-coating layers and smooth-coating layers were further applied on the surface of the core portion for the purpose of to make the surface into complete spherical form and smooth. Then the surface of thus obtained multi-layer tablets was treated by color coating until the desired color was obtained. The multi-layer tablets were dried and polished the surface thereof so as to make them tablets having uniform brilliance.

| Example of preparation of multi-layer tablets - 2 | |
| --- | --- |
| 5-(5-Methoxy-2-benzimidazolyl)sulfinyl-3-methyl-5,6,7,8-tetrahydroquinoline | 150.0 g |
| Citric acid | 1.0 g |
| Lactose | 33.5 g |
| Calcium secondary phosphate | 70.0 g |
| Pluronic F-68 (Trademark for a nonionic series of polyoxyalkylene derivative of propylene glycol, manufactured by BASF-Wyandotte Corp.) | 30.0 g |
| Sodium laurylsulfate | 15.0 g |
| Polyvinyl pyrrolidone | 15.0 g |

-continued

| Example of preparation of multi-layer tablets - 2 | |
|---|---|
| Polyethylene glycol (Carbowax 1500, manufactured by Union Carbide Corp.) | 4.5 g |
| Polyethylene glycol (Carbowax 6000, manufactured by Union Carbide Corp.) | 45.0 g |
| Corn starch | 30.0 g |
| Dried sodium laurylsulfate | 3.0 g |
| Dried magnesium stearate | 3.0 g |
| Ethanol | q.s. |

By procedures similar to those described in the above-mentioned Example of preparation of multi-layer tablets-1, there were prepared multi-layer tablets having the above-mentioned formulation.

| Example of preparation of multi-layer tablets - 3 | |
|---|---|
| 5-Methyl-2-[(3,5-dimethyl-4-methoxy-2-pyridyl)methylthio]imidazo[4,5-b]-pyridine | 150.0 g |
| Citric acid | 1.0 g |
| Lactose | 33.5 g |
| Calcium secondary phosphate | 70.0 g |
| Pluronic F-68 (Trademark for a nonionic series of polyoxyalkylene derivative of propylene glycol, manufactured by BASF-Wyandotte Corp.) | 30.0 g |
| Sodium laurylsulfate | 15.0 g |
| Polyvinylpyrrolidone | 15.0 g |
| Polyethylene glycol (Carbowax 1500, manufactured by Union Carbide Corp.) | 4.5 g |
| Polyethylene glycol (Carbowax 6000, manufactured by Union Carbide Corp.) | 45.0 g |
| Corn starch | 30.0 g |
| Dried sodium laurylsulfate | 3.0 g |
| Dried magnesium stearate | 3.0 g |
| Ethanol | q.s |

By procedures similar to those described in the above-mentioned Example of preparation of multi-layer tablets-1, there were prepared multi-layer tablets having the above-mentioned formulation.

| Example of preparation of injection solution - 1 | |
|---|---|
| 4-Allyloxy-8-(2-benzimidazolyl)sulfinyl-3-methyl-5,6,7,8-tetrahydroquinoline | 5.0 g |
| Polyethylene glycol (Molecular weight: 4000) | 0.3 g |
| Sodium chloride | 0.9 g |
| Polyoxyethylene sorbitan monooleate | 0.4 g |
| Sodium metabisulfite | 0.1 g |
| Methyl para-hydroxybenzoate | 0.18 g |
| Propyl para-hydroxybenzoate | 0.02 g |
| Distilled water for injection | 10.0 ml |

Into a half volume of the above-mentioned distilled water for injection, methyl para-hydroxybenzoate, propyl para-hydroxybenzoate, sodium metabisulfite and sodium chloride were dissolved under stirring at 80° C. The solution thus obtained was cooled to 40° C., then 4-allyloxy-8-(2-benzimidazolyl)sulfinyl-3-methyl-5,6,7,8-tetrahydroquinoline, next polyethylene glycol and polyoxyethylene sorbitan monooleate were dissolved therein. Then the remaining volume of the distilled water for injection was added to the solution so as to adjust the final volume of the preparation, then sterilized the obtained injection solution by using a suitable filter paper to make the desired injection preparation.

| Example of preparation of injection solution - 2 | |
|---|---|
| 8-(5-Methoxy-2-benzimidazolyl)sulfinyl-5,6,7,8-tetrahydroquinoline | 5.0 g |
| Polyethylene glycol (Molecular weight: 4000) | 0.3 g |
| Sodium chloride | 0.9 g |
| Polyoxyethylene sorbitan monooleate | 0.4 g |
| Sodium metabisulfite | 0.1 g |
| Methyl para-hydroxybenzoate | 0.18 g |
| Propyl para-hydroxybenzoate | 0.02 g |
| Distilled water for injection | 10.0 ml |

By procedures similar to those described in the above-mentioned Example of preparation of injection solution-1, there was prepared injection solution having the above-mentioned formulation.

| Example of preparation of injection solution - 3 | |
|---|---|
| 5-Chloro-2-[(3,5-dimethyl-4-methoxy-2-pyridyl)methylthio]imidazo[4,5-b]-pyridine | 5.0 g |
| Polyethylene glycol (Molecular weight: 4000) | 0.3 g |
| Sodium chloride | 0.9 g |
| Polyoxyethylene sorbitan monooleate | 0.4 g |
| Sodium metabisulfite | 0.1 g |
| Methyl para-hydroxybenzoate | 0.18 g |
| Propyl para-hydroxybenzoate | 0.02 g |
| Distilled water for injection | 10.0 ml |

By procedures similar to those described in the above-mentioned Example of preparation of injection solution-1, there was prepared injection solution having the above-mentioned formulation.

REFERENCE EXAMPLE 1

6.5 Grams of 3-methyl-5,6,7,8-tetrahydroquinoline-N-oxide was added dropwise in a mixture consisting of 7 ml of fuming nitric acid and 7 ml of concentrated sulfuric acid under ice-cooled condition with stirring. The reaction mixture was stirred at 40° C. for 2 hours, then further stirred at 60° C. for 2 hours. The reaction mixture was poured in a cold aqueous solution of sodium hydroxide, then extracted with chloroform. The chloroform layer was washed with an aqueous solution saturated with sodium chloride, then dried with anhydrous magnesium sulfate. Chloroform was removed by evaporation, and the thus obtained residue was recrystallized from ethyl acetate-ethanol-n-hexane to yield 5.3 g of 3-methyl-4-nitro-5,6,7,8-tetrahydroquinoline-N-oxide.

Melting point: 140°–142° C.

REFERENCE EXAMPLE 2

2.0 Grams of 3-methyl-4-nitro-5,6,7,8tetrahydroquinoline-N-oxide was dissolved in allyl alcohol. Then 0.6 g of sodium hydroxide was added thereto, and the mixture was stirred at 70°–80° C. for 3 hours. After the reaction was completed, the reaction mixture was concentrated under reduced pressure, to the residue thus obtained was added water, and was extracted with chloroform. The chloroform layer was washed with an aqueous solution saturated with sodium chloride, then dried with anhydrous magnesium sulfate. Chloroform was removed by evaporation under reduced pressure to obtain 1.4 g of 4-allyloxy-3-methyl-5,6,7,8-tetrahydroquinoline-N-oxide in the form of brown oily substance.

NMR (CDCl$_3$) δ: 1.50–2.10 (m, 4H), 2.21 (s, 3H), 2.80 (t, 2H), 2.89 (t, 2H), 4.00–4.50 (m, 2H), 4.90–5.50 (m, 2H), 5.80–6.30 (m, 1H), 8.00 (s, 1H).

REFERENCE EXAMPLE 3

To 4.8 g of 4-allyloxy-3-methyl-5,6,7,8-tetrahydroquinoline-N-oxide was added 50 ml of acetic anhydride, and the mixture was stirred at 90° C. for 5 hours. After the reaction was completed, acetic anhydride was removed by evaporation under reduced pressure, to the residue thus obtained was added water and then extracted with chloroform. The chloroform layer was washed with an aqueous solution of sodium hydroxide and an aqueous solution saturated with sodium chloride, then dried with anhydrous magnesium sulfate. Chloroform was removed by evaporation under reduced pressure to obtain 5.0 g of 8-acetoxy-4-allyloxy-3-methyl-5,6,7,8-tetrahydroquinoline in the form of brown oily substance.

NMR (CDCl$_3$) δ: 1.70–2.20 (m, 4H), 2.25 (s, 3H), 2.50–3.00 (m, 2H), 4.30–4.50 (m, 2H), 5.20–5.60 (m, 2H), 5.91 (t, 1H), 5.80–6.40 (m, 1H), 8.30 (s, 1H).

REFERENCE EXAMPLE 4

5.0 Grams of 8-acetoxy-4-allyloxy-3-methyl-5,6,7,8-tetrahydroquinoline was dissolved in 20 ml of methanol. Then a solution prepared by dissolving 2.3 g of sodium hydroxide in 20 ml of water was added thereto, and the mixture was refluxed for 1 hour. After the reaction was completed, methanol was removed by evaporation, and to the residue thus obtained was added water, and was extracted with chloroform. The chloroform layer was washed with an aqueous solution saturated with sodium chloride, then dried with anhydrous magnesium sulfate. Chloroform was removed by evaporation to obtain 3.5 g of 4-allyloxy-8-hydroxy-3-methyl-5,6,7,8-tetrahydroquinoline in the form of brown oily substance.

NMR (CDCl$_3$) δ: 1.50–2.50 (m, 4H), 2.21 (s, 3H), 2.73 (t, 2H), 4.30–4.50 (m, 2H), 4.67 (t, 1H), 5.10–5.60 (m, 2H), 5.80–6.30 (m, 1H), 8.21 (s, 1H).

REFERENCE EXAMPLE 5

3.5 Grams of 4-allyloxy-8-hydroxy-3-methyl-5,6,7,8-tetrahydroquinoline was dissolved in 40 ml of chloroform, to this solution was added dropwise a solution consisting of 2.8 g of phosphorus tribromide and 5 ml of chloroform under ice-cooled condition. The reaction mixture was stirred under ice-cooled condition for 2 hours, further stirred at room temperature for 2 hours. The reaction mixture was poured into a cold sodium hydroxide aqueous solution, then extracted with chloroform. The chloroform layer was washed with an aqueous solution saturated with sodium chloride, then dried with anhydrous magnesium sulfate. Chloroform was removed by evaporation, then the residue thus obtained was purified by a silica gel column chromatography (eluent: methylene chloride/methanol=100/1) to obtain 1.3 g of 4-allyloxy-8-bromo-3-methyl-5,6,7,8-tetrahydroquinoline.

NMR (CDCl$_3$) δ: 1.60–3.20 (m, 6H), 2.23 (s, 3H), 4.30–4.50 (m, 2H, 5.20–5.60 (m, 3H), 5.80–6.30 (m, 1H), 8.29 (s, 1H).

REFERENCE EXAMPLE 6

7.02 Grams of 3-methyl-5,6,7,8-tetrahydroquinoline-N-oxide was dissolved in acetic anhydride, and the solution was heated at 90° C. with stirring for 3.5 hours. Acetic anhydride was removed by evaporation under reduced pressure, then an aqueous solution of sodium carbonate was added to make the residue alkaline and was extracted with chloroform. The chloroform layer was washed with an aqueous solution saturated with sodium chloride, then dried with anhydrous magnesium sulfate. The solvent was removed by evaporation, and the residue thus obtained was purified by a silica gel column chromatography (eluent:dichloromethane) to obtain 7.18 g of 3-methyl-8-acetoxy-5,6,7,8-tetrahydroquinoline.

NMR (CDCl$_3$) δ: 1.60–2.30 (m, 4H), 2.10 (s, 3H), 2.30 (s, 3H), 2.60–2.90 (m, 2H), 5.92 (t, 1H), 7.26 (d, 1H), 8.33 (d, 1H)

REFERENCE EXAMPLE 7

1.50 Grams of 3-methyl-8-hydroxy-5,6,7,8-tetrahydroquinoline was dissolved in 20 ml of chloroform, to this solution was added dropwise a solution consisting of 1.35 g of phosphorus tribromide and 5 ml of chloroform under ice-cooled condition, then the mixture was stirred under ice-cooled condition for 2 hours, next was stirred at room temperature overnight. To the reaction mixture was added 5%-sodium hydroxide aqueous solution, then was extracted with chloroform. The chloroform layer was washed with an aqueous solution saturated with sodium chloride, and dried with anhydrous magnesium sulfate. The solvent was removed by evaporation to obtain 1.80 g of 3-methyl-8-bromo-5,6,7,8-tetrahydroquinoline.

NMR (CDCl$_3$) δ: 1.80–2.60 (m, 4H), 2.28 (s, 3H), 2.60–3.00 (m, 2H), 5.50–5.60 (m, 1H), 7.23 (d, 1H), 8.30 (d, 1H).

REFERENCE EXAMPLE 8

4.11 Grams of 3-methyl-8-acetoxy-5,6,7,8-tetrahydroquinoline was dissolved in 15 ml of 30%-sodium hydroxide aqueous solution and 15 ml of methanol, the thus obtained mixture was stirred with heating at 65° C. for 3 hours. The solvent was removed by evaporation, and the residue thus obtained was purified by a silica gel column chromatography (eluent: n-hexane/ethyl acetate=5/1) to obtain 1.50 g of 3-methyl-8-hydroxy-5,6,7,8-tetrahydroquinoline.

NMR (CDCl$_3$) δ: 1.50–2.50 (m, 4H), 2.27 (s, 3H), 2.73 (t, 2H), 4.65 (t, 1H), 7.23 (d, 1H), 8.25 (d, 1H).

REFERENCE EXAMPLE 9

To 7.02 g of 3-methyl-5,6,7,8-tetrahydroquinoline was added dropwise 9.62 g of methanesulfonyl chloride under ice-cooled condition. The reaction mixture was stirred under ice-cooling condition for 2 hours, then further stirred at 80° C. for 3 hours. To the reaction mixture was added water, and this solution was made alkaline by adding sodium carbonate, then extracted with diethyl ether. The diethyl ether layer was washed with an aqueous solution saturated with sodium chloride, and dried with anhydrous magnesium sulfate. The solvent was removed by evaporation, then thus obtained residue was purified by a silica gel column chromatography (eluent: dichloromethane/methanol=100/1) to obtain 2.74 g of 3-methyl-8-chloro-5,6,7,8-tetrahydroquinoline.

NMR (CDCl$_3$) δ: 1.70–2.50 (m, 4H), 2.30 (s, 3H), 2.50–3.00 (m, 2H), 5.28 (t, 1H), 7.23 (d, 1H), 8.32 (d, 1H).

REFERENCE EXAMPLE 10

0.97 Gram of 7,8-dihydro-3-methylquinolin-5(6H)-one was dissolved in 20 ml of methanol, then to this solution was added 0.23 g of sodium borohydride under ice-cooled condition, the mixture was stirred at room temperature for 3 hours. To the reaction mixture was added water, then methanol was removed by evaporation, next extracted with chloroform, and the chloroform extract was dried with anhydrous magnesium sulfate. The solvent was removed by evaporation to obtain 0.98 g of 3-methyl-5-hydroxy-5,6,7,8-tetrahydroquinoline in the form of colorless oily substance.

NMR (CDCl$_3$) δ: 1.60–2.20 (m, 4H), 2.27 (s, 3H), 2.83 (t, 2H), 3.28 (bs, 1H), 4.7–4.8 (m, 1H), 7.57 (d, 1H), 8.15 (d, 1H).

REFERENCE EXAMPLE 11

By procedures similar to those described in Reference Example 7, by using a suitable starting material, there was prepared the following compound. 3-Methyl-5-bromo-5,6,7,8-tetrahydroquinoline NMR (CDCl$_3$) δ: 1.80–2.50 (m, 4H), 2.28 (s, 3H), 2.80–3.20 (m, 2H0, 5.43 (t, 1H), 7.43 (bs, 1H), 8.25 (bs, 1H).

REFERENCE EXAMPLE 12

23 Grams of methyl 6-chloro-5-nitronicotinate was dissolved in 200 ml of dioxane. To this solution was introduced ammonia gas under stirring condition at room temperature. 10 Minutes after the introduction of ammonia gas, the crystals formed in the reaction mixture were collected by filtration. Recrystallized from dimethylformamide (DMF) to yield 18 g of methyl 6-amino-5-nitronicotinate in the form of yellow needle-like crystals. Melting point: 195°–196° C.

REFERENCE EXAMPLE 13

1 Gram of methyl 6-amino-5-nitronicotinate was dissolved in 10 m of methanol. To this solution was added 0.1 g of 5%-palladium-carbon, then hydrogen gas was absorbed at room temperature under a normal pressure. The reaction was stopped when the stoichiometric amount of hydrogen was absorbed. The catalyst was removed from the reaction mixture by filtration, and the solvent was removed by evaporation. The residue thus obtained was recrystallized from ethanol to yield 0.8 g of methyl 5,6-diaminonicotinate in the form of yellow needle-like crystals. Melting point: 154°–155° C.

REFERENCE EXAMPLE 14

0.2 Gram of methyl 5,6-diaminonicotinate was dissolved in 5 ml of dimethylformamide, to this solution was added 1.2 ml of carbon disulfide, then the mixture was stirred at room temperature for 18 hours. The solvent was removed by evaporation, the residue thus obtained was recrystallized from dimethylformamide to obtain 0.2 g of 2-mercapto-5-methoxycarbonylimidazo[4,5-b]pyridine in the form of yellow powdery substance. Melting point: 233°–234° C.

REFERENCE EXAMPLES 15–20

By procedures similar to those described in Reference Example 14, by using suitable starting material, there were prepared the compounds as shown in Table 1 below.

TABLE 1

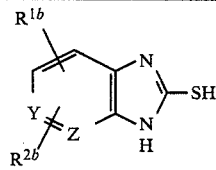

| Reference Example No. | Y | Z | R$^{1b}$ | R$^{2b}$ | Melting point (°C.) | Recrystallization solvent | Crystal form |
|---|---|---|---|---|---|---|---|
| 15 | CH | N | 5-CH$_3$ | H | 328–330 | Ethanol | Yellow powdery substance |
| 16 | CH | N | 5-Cl | H | 122–124 | Dimethylformamide | Yellow powdery substance |
| 17 | CH | N | 5-Br | 4-CH$_3$ | 228–229 | Ethanol | Yellow powdery substance |
| 18 | CH | N | 5-Br | 6-CH$_3$ | Over 300 | Ethanol | Yellow powdery substance |
| 19 | CH | N | H | 6-NH$_3$ | Over 300 | Ethanol | Green powdery substance |
| 20 | CH | N | 5-NH$_2$ | H | Over 300 | Ethanol | Red powdery substance |

EXAMPLE 1

0.5 Gram of 2-mercaptobenzimidazole was dissolved in 30 ml of methanol, and to this solution was added an aqueous solution prepared by dissolving 0.2 g of sodium hydroxide in 10 ml of water and further added 0.6 g of 4-allyloxy-8-bromo-3-methyl-5,6,7,8-tetrahydroquinoline, then the whole mixture was refluxed for 2 hours. Methanol was removed from the reaction mixture by evaporation, and to the residue thus obtained was added water and then extracted with chloroform. After the chloroform extract was dried with anhydrous magnesium sulfate, then chloroform was removed by evaporation, the residue thus obtained was purified by a silica gel column chromatography (eluent: methylene chloride/methanol=100/1) to obtain 0.7 g of 4-allyloxy-8-(2-benzimidazoyl)thio-3-methyl-5,6,7,8-tetrahydroquinoline in the form of light brown oily substance.

NMR (CDCl$_3$) δ: 1.70–2.10 (m, 2H), 2.10–2.50 (m, 2H), 2.29 (s, 3H), 2.60–3.10 (m, 2H), 4.30–4.50 (m, 2H), 4.77 (t, 1H), 5.20–5.60 (m, 2H), 5.80–6.50 (m, 1H), 7.10–7.30 (m, 2H), 7.40–7.70 (m, 2H), 8.33 (s, 1H).

EXAMPLES 2-14

By procedures similar to those described in Example 1, by using suitable starting materials, there were prepared compounds of Examples 2-14 as follows.

reaction was completed, the reaction mixture was washed with as aqueous solution of sodium carbonate, and dried with anhydrous magnesium sulfate. Methylene chloride was removed by evaporation under reduced pressure, the residue thus obtained was recrystal-

TABLE 2

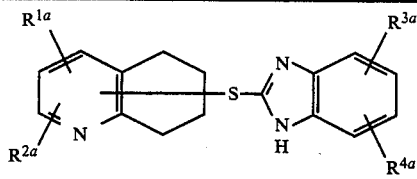

| Example No. | $R^{1a}$ | $R^{2a}$ | $R^{3a}$ | $R^{4a}$ | Substituted position of the group of —S—W* | Appearance of the product |
|---|---|---|---|---|---|---|
| 2 | 3-$CH_3$ | 4-$OCH_2CH=CH_2$ | 5-F | H | 8 | Light brown oily substance[1] |
| 3 | 3-$CH_3$ | 4-$OCH_2CH=CH_2$ | 5-$CH_3$ | 5-$CH_3$ | 8 | Light brown oily substance[2] |
| 4 | 3-$CH_3$ | 4-$OCH_2CH=CH_2$ | 4-$CH_3$ | H | 8 | Light brown oily substance[3] |
| 5 | 3-$CH_3$ | 4-$OCH_2CH=CH_2$ | 5-F | 6-$OCH_3$ | 8 | Light brown oily substance[4] |
| 6 | 3-$CH_3$ | 4-$OCH_2CH=CH_2$ | 5-F | 6-F | 8 | Light brown oily substance[5] |
| 7 | 3-$CH_3$ | 4-$OCH_2$—$CH_2OCH_3$ | 5-F | H | 8 | Light brown oily substance[6] |
| 8 | 3-$CH_3$ | 4-$OCH_2$—C≡CH | H | H | 8 | Light brown oily substance[7] |
| 9 | 3-$CH_3$ | 4-$OCH_2C$≡CH | 5-F | H | 8 | Light brown oily substance[8] |
| 10 | 3-$CH_3$ | 4-$OCH_2C$≡CH | 5-$CH_3$ | 6-$CH_3$ | 8 | Light brown oily substance[9] |
| 11 | 3-$CH_3$ | 4-$OCH_2$—$CH_2OCH_3$ | H | H | 8 | Light brown oily substance[10] |
| 12 | 3-$CH_3$ | 4-$OCH_2CH=CH_2$ | 5-Cl | 6-Cl | 8 | Light brown oily substance[11] |
| 13 | 3-$CH_3$ | 4-$OCH_2C$≡CH | 5-Cl | 6-Cl | 8 | Light brown oily substance[12] |
| 14 | H | 4-$OCH_2C$≡CH | 5-F | H | 8 | Light brown oily substance[13] |

W* is a group of the formula: 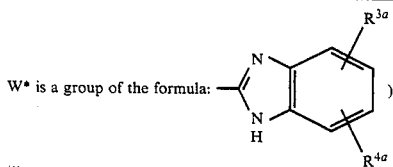

[1] NMR ($CDCl_3$) δ: 1.50-2.20 (m, 2H), 2.20-2.50 (m, 2H), 2.30 (s, 3H), 2.60-3.00 (m, 2H), 4.30-4.50 (m, 2H), 4.73 (t, 1H), 5.20-5.60 (m, 2H), 5.80-6.40 (m, 1H), 6.70-7.10 (m, 1H), 7.10-7.60 (m, 2H), 8.33 (s, 1H).

[2] NMR ($CDCl_3$) δ: 1.70-2.10 (m, 2H), 2.10-2.50 (m, 2H), 2.27 (s, 3H), 2.33 (s, 6H), 2.60-3.10 (m, 2H), 4.30-4.50 (m, 2H), 4.70 (t, 1H), 5.20-5.60 (m, 2H), 5.80-6.40 (m, 1H), 7.33 (s, 2H), 8.33 (s, 1H).

[3] NMR ($CDCl_3$) δ: 1.60-2.10 (m, 2H), 2.10-2.50 (m, 2H), 2.30 (s, 3H), 2.63 (s, 3H), 2.60-3.10 (m, 2H), 4.30-4.50 (m, 2H), 4.73 (t, 1H), 5.20-5.60 (m, 2H), 5.70-6.50 (m, 1H), 6.90-7.30 (m, 2H), 7.30-7.60 (m, 1H), 8.33 (s, 1H).

[4] NMR ($CDCl_3$) δ: 1.60-2.10 (m, 2H), 2.10-2.50 (m, 2H), 2.30 (s, 3H), 2.60-3.10 (m, 2H), 3.92 (s, 3H), 4.30-4.50 (m, 2H), 4.87 (t, 1H), 5.20-5.60 (m, 2H), 5.80-6.40 (m, 1H), 7.10 (d, 1H), 7.30 (d, 1H), 8.33 (s, 1H).

[5] NMR ($CDCl_3$) δ: 1.60-2.10 (m, 2H), 2.10-2.50 (m, 2H), 2.30 (s, 3H), 2.60-3.10 (m, 2H), 4.40-4.50 (m, 2H), 4.38 (t, 1H), 5.20-5.60 (m, 2H), 5.80-6.40 (m, 1H), 7.10-7.50 (m, 2H), 8.30 (s, 1H).

[6] NMR ($CDCl_3$) δ: 1.80-2.04 (m, 2H), 2.16-2.48 (m, 2H), 2.31 (s, 3H), 2.60-3.06 (m, 2H), 3.46 (s, 3H), 3.66-3.80 (m, 2H), 4.00-4.14 (m, 2H), 4.76 (t, 1H), 6.94 (dt, 1H), 7.24 (dd, 1H), 7.46 (dd, 1H), 8.32 (s, 1H).

[7] NMR ($CDCl_3$) δ: 1.80-2.04 (m, 2H), 2.20-2.44 (m, 2H), 2.32 (s, 3H), 2.55 (t, 1H), 2.64-3.12 (m, 2H), 4.65 (d, 2H), 4.80 (t, 1H), 7.12-7.28 (m, 2H), 7.48-7.64 (m, 2H), 8.34 (s,1H).

[8] NMR ($CDCl_3$) δ: 1.80-2.07 (m, 2H), 2.23-2.50 (m, 2H), 2.31 (s, 3H), 2.56 (t, 1H), 2.63-3.10 (m, 2H), 4.64 (d, 2H), 4.81 (t, 1H), 6.91 (dt, 1H), 7.25 (dd, 1H), 7.43 (dd, 1H), 8.32 (s, 1H).

[9] NMR ($CDCl_3$) δ: 1.71-1.94 (m, 2H), 2.14-2.37 (m, 2H), 2.25 (s, 3H), 2.30 (s, 6H), 2.54 (t, 1H), 2.57-3.00 (m, 2H), 4.55 (d, 2H), 4.80 (t, 1H), 7.30 (s, 2H), 8.27 (s, 1H).

[10] NMR ($CDCl_3$) δ: 1.80-2.00 (m, 2H), 2.20-2.48 (m, 2H), 2.30 (s, 3H), 2.60-3.04 (m, 2H), 3.45 (s, 3H), 3.64-3.80 (m, 2H), 3.96-4.20 (m, 2H), 4.76 (t, 1H), 7.08-7.28 (m, 2H), 7.44-7.68 (brs, 2H), 8.33 (s, 1H).

[11] NMR ($CDCl_3$) δ: 1.70-2.10 (m, 2H), 2.10-2.50 (m, 2H), 2.30 (s, 3H), 2.70-3.00 (m, 2H), 4.40-4.50 (m, 2H), 4.77 (t, 1H), 5.20-5.60 (m, 2H), 5.80-6.30 (d, 1H), 7.60 (s, 2H), 8.30 (s, 1H).

[12] NMR ($CDCl_3$) δ: 1.72-2.16 (m, 2H), 2.24-2.48 (m, 2H), 2.34 (s, 3H), 2.57 (t, 1H), 2.60-3.08 (m, 2H), 4.68 (d, 2H), 4.80 (t, 1H), 7.63 (s, 2H), 8.33 (s, 1H).

[13] NMR ($CDCl_3$) δ: 1.70-2.10 (m, 2H), 2.20-2.50 (m, 2H), 2.50-2.90 (m, 3H), 4.60-4.90 (m, 2H), 6.60-7.50 (m, 3H) 6.83 (d,1H), 8.38 (d, 1H).

EXAMPLE 15

0.7 Gram of 4-allyloxy-8(2-benzimidazolyl)thio-3-methyl-5,6,7,8-tetrahydroquinoline was dissolved in 30 ml of methylene chloride, then this solution was cooled to −50° to −60° C., next to this solution was added dropwise a solution prepared by dissolving 0.43 g of 80%-meta-chloroperbenzoic acid in 10 ml of methylene chloride, and the reaction mixture was stirred for 20 minutes at the above mentioned temperature. After the lized from diethyl ether to obtain 0.4 g of 4-allyloxy-8-(2-benzimidazolyl)sulfinyl-3-methyl-5,6,7,8-tetrahydroquinoline. White powdery crystals. Melting point: 100°-102° C. (decomposed)

EXAMPLES 16-28

By methods similar to those described in Example 15, and using suitable starting materials there were prepared compounds of Examples 16–28 as shown in Table 3 as follows.

TABLE 3

| Example No. | $R^{1a}$ | $R^{2a}$ | $R^{3a}$ | $R^{4a}$ | Substituted position of the formula —S—W* ↓ O | Crystal form (Recrystallization solvent) | Melting point (°C.) |
|---|---|---|---|---|---|---|---|
| 16 | 3-$CH_3$ | 4-$OCH_2CH=CH_2$ | 5-F | H | 8 | Light yellow powdery crystals (Petroleum ether) | 60–64 (decomposed) |
| 17 | 3-$CH_3$ | 4-$OCH_2CH=CH_2$ | 5-$CH_3$ | 6-$CH_3$ | 8 | Light yellow powdery crystals (Petroleum ether) | 89–91 (decomposed) |
| 18 | 3-$CH_3$ | 4-$OCH_2CH=CH_2$ | 4-$CH_3$ | H | 8 | White powdery crystals (Diethyl ether-n-hexane) | 47–51 (decomposed) |
| 19 | 3-$CH_3$ | 4-$OCH_2CH=CH_2$ | 5-F | 6-$OCH_3$ | 8 | Light brown powdery crystals (Diethyl ether) | 110–112 (decomposed) |
| 20 | 3-$OCH_3$ | 4-$OCH_2CH=CH_2$ | 5-F | 6-F | 8 | Yellow brown powdery crystals (Diethyl ether) | 18–120 (decomposed) |
| 21 | 3-$CH_3$ | 4-$OCH_2-CH_2OCH_3$ | 5-F | H | 8 | White powdery crystals (Diethyl ether) | 103.5–104.5 (decomposed) |
| 22 | 3-$CH_3$ | 4-$OCH_2-C\equiv CH$ | H | H | 8 | White powdery crystals (Diethyl ether) | 105–106.5 (decomposed) |
| 23 | 3-$CH_3$ | 4-$OCH_2-C\equiv CH$ | 5-F | H | 8 | White powdery crystals (Diethyl ether -petroleum ether) | 100–101 (decomposed) |
| 24 | 3-$CH_3$ | 4-$OCH_2-C\equiv CH$ | 5-$CH_3$ | 6-$CH_3$ | 8 | White powdery crystals (Diethyl ether) | 110–111 (decomposed) |
| 25 | 3-$CH_3$ | 4-$OCH_2-CH_2OCH_3$ | H | H | 8 | Yellow powdery crystals (Diethyl ether) | 89.5–90.5 (decomposed) |
| 26 | 3-$CH_3$ | 4-$OCH_2CH=CH_2$ | 5-Cl | 6-Cl | 8 | Light yellow powdery crystals (Petroleum ether) | 96–98 (decomposed) |
| 27 | 3-$CH_3$ | 4-$OCH_2-C\equiv CH$ | 5-Cl | 6-Cl | 8 | Yellowish white powdery crystals (Diethyl ether) | 122.5–123.5 (decomposed) |
| 28 | H | 4-$OCH_2-C\equiv CH$ | 5-F | H | 8 | White powdery crystals (Diethyl ether) | 120–121 (decomposed) |

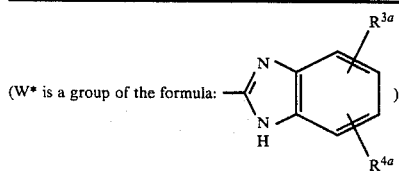

(W* is a group of the formula: )

EXAMPLE 29

0.46 Gram of 2-chlorobenzimidazole, 0.2 g of thiourea and 10 ml of ethanol were mixed together and the mixture was refluxed for 2 hours. To this reaction mixture was added 0.62 g of 4-allyloxy-8-bromo-3-methyl-5,6,7,8-tetrahydroquinoline and 0.3 g of sodium hydroxide, then the whole reaction mixture was refluxed for 5 hours. After the reaction was completed, ethanol was removed by evaporation, and to the residue thus obtained was added water and then extracted with chloroform, and the chlorofrom extract was dried with anhydrous magnesium sulfate, and chloroform was removed by evaporation. The residue thus obtained was purified by means of a silica gel column chromatography (eluent: methylene chloride/methanol=100/1) to obtain 0.5 g of 4-allyloxy-8-(2-benzimidazolyl)thio-3-methyl-5,6,7,8-tetrahydroquinoline in the form of light brown oily substance.

NMR (CDCl$_3$) δ: 1.70–2.10 (m, 2H), 2.10–2.50 (m, 2H), 2.29 (s, 3H), 2.60–3.10 (m, 2H), 4.30–4.50 (m, 2H), 4.77 (t, 1H), 5.20–5.60 (m, 2H), 5.80–6.50 (m, 1H), 7.10–7.30 (m, 2H), 7.40–7.70 (m, 2H), 8.33 (s, 1H).

By a procedure similar to that described in Example 29, by using suitable starting material, there were prepared compounds of the above-mentioned Examples 2–14.

EXAMPLE 30

4.00 Grams of 3-methyl-8-(5-methoxy-2-benzimidazolyl)thio-5,6,7,8-tetrahydroquinoline was dissolved in 80 ml of dichloromethane, to this solution was added dropwise slowly at −10° C. a solution which was prepared by dissolving 2.37 g of meta-chloroperbenzoic acid (85%) in 30 ml of dichloromethane. After the dropwise addition was finished, the reaction mixture was stirred at −10° C. to −4° C. for 15 minutes. Water was added to the reaction mixture, then was made alkaline by adding sodium carbonate, then extracted with diethyl ether. The diethyl ether layer was washed with an aqueous solution saturated with sodium chloride, then was dried with anhydrous magnesium sulfate. The solvent was removed from the extract by evaporation, and was recrystallized from dichlomethane-diethyl ether to obtain 2.30 g of 3-methyl-8-(5-methoxy-2-benzimidazolyl)sulfinyl-5,6,7,8-tetrahydroquinoline in the form of white powdery crystals. Melting point: 114°–114.5° C. (decomposed).

EXAMPLES 31–64

By a method similar to that described in Example 30, by using suitable starting materials, there were prepared compounds of Examples 31–64 as shown in the following Table 4.

TABLE 4

| Example No. | $R^{1a}$ | $R^{2a}$ | $R^{3a}$ | $R^{4a}$ | Substituted position of the formula —S—W* ↓ O | Crystal form (Recrystallization solvent) | Melting point (°C.) |
|---|---|---|---|---|---|---|---|
| 31 | H | H | 5-OCH$_3$ | H | 8 | White powdery crystals (Ethyl acetate) | 114.5–115.5 (decomposed) (monohydrate) |
| 32 | H | H | 5-CF$_3$ | H | 8 | Brown indefinite form crystals (14) | — |
| 33 | H | H | H | H | 8 | Colorless prism-like crystals (Methylene chloride-diethyl ether) | 119–120.5 (decomposed) |
| 34 | H | H | 5-CH$_3$ | H | 8 | White powdery crystals (Methylene chloride-diethyl ether) | 122–123 (decomposed) |
| 35 | H | H | 5-Cl | H | 8 | Light brown powdery crystals (Diethyl ether) | 115–116 (decomposed) |
| 36 | H | H | 5-OCH$_3$ | 6-OCH$_3$ | 8 | White powdery crystals (Ethyl acetate) | 125–127 (decomposed) |
| 37 | 3-CH$_3$ | H | H | H | 8 | Yellow indefinite form crystals (15) | — |
| 38 | 3-CH$_3$ | H | 5-CH$_3$ | H | 8 | Yellow indefinite form crystals (16) | — |
| 39 | 3-CH$_3$ | H | 5-COCH$_3$ | H | 8 | Brown oily substance (17) | — |
| 40 | 3-CH$_3$ | H | 5-OCH$_3$ | 6-OCH$_3$ | 8 | Light yellow powdery crystals (Methylene chloride-diethyl ether) | 121–123 (decomposed) |
| 41 | H | 4-CH$_3$ | 5-OCH$_3$ | H | 8 | Yellow indefinite form crystals (18) | — |
| 42 | H | 2-CH$_3$ | 5-OCH$_3$ | H | 8 | Brown indefinite form crystals (19) | — |
| 43 | H | 4-OCH$_3$ | 5-OCH$_3$ | H | 8 | Colorless oily substance (20) | — |
| 44 | H | 4-OCH$_3$ | 5-CF$_3$ | H | 8 | Light yellow powdery crystals (Methylene chloride-diethyl ether) | 140–142 (decomposed) |
| 45 | H | 2-Cl | 5-OCH$_3$ | H | 8 | Colorless needle-like crystals (Ethyl acetate) | 121.5–123.5 (decomposed) |
| 46 | 3-CH$_3$ | 2-Cl | 5-OCH$_3$ | H | 8 | White powdery crystals (Ethyl acetate) | 116–117 (decomposed) (½ hydrate) |
| 47 | 3-CH$_3$ | H | 5-CF$_3$ | H | 8 | Yellow indefinite | — |

TABLE 4-continued

Structure: benzimidazole with R³ᵃ, R⁴ᵃ substituents connected via S(=O) to a substituted ring bearing R¹ᵃ, R²ᵃ.

| Example No. | R¹ᵃ | R²ᵃ | R³ᵃ | R⁴ᵃ | Substituted position of the formula —S—W* ↓ O | Crystal form (Recrystallization solvent) | Melting point (°C.) |
|---|---|---|---|---|---|---|---|
| 48 | 3-CH₃ | H | 5-OCH₃ | H | 5 | form crystals (21) Colorless oily substance (22) | — |
| 49 | 3-CH₃ | H | 5-CF₃ | H | 5 | Colorless indefinite form crystals (23) | — |
| 50 | H | H | 5-NO₂ | H | 8 | Light brown powdery crystals (Ethyl acetate-ethanol-n-hexane) | 152–154 (decomposed) |
| 51 | H | H | 5-CH₃ | 6-CH₃ | 8 | White powdery crystals (Methylene chloride-diethyl ether) | 141–142 (decomposed) |
| 52 | H | H | H | 4-CH₃ | 8 | White powdery crystals (Diethyl ether) | 113–114 (decomposed) |
| 53 | H | H | 5-F | H | 8 | White powdery crystals (Diethyl ether) | 118–119 (decomposed) |
| 54 | H | 2-OH | 5-OCH₃ | H | 8 | White powdery crystals (Ethyl acetate-n-hexane) | 117.5–118.5 (decomposed) |
| 55 | 3-CH₃ | 4-OCH₃ | 5-F | H | 8 | White powdery crystals (Methylene chloride-diethyl ether) | 117–118 (decomposed) |
| 56 | 3-CH₃ | 4-OCH₃ | H | H | 8 | Light brown powdery crystals (Methylene chloride-diethyl ether) | 102.5–104 (decomposed) |
| 57 | 3-CH₃ | 4-OCH₃ | 5-CH₃ | 6-CH₃ | 8 | White powdery crystals (Diethyl ether) | 119–120 (decomposed) |
| 58 | H | H | 5-Cl | 6-Cl | 8 | Light brown powdery crystals (Methylene chloride diethyl ether) | 141.5–142.5 (decomposed) |
| 59 | H | H | 5-OC₂H₅ | 6-F | 8 | White powdery crystals (Methylene chloride-diethyl ether) | 128–129.5 (decomposed) |
| 60 | H | H | 5-F | 6-F | 8 | White powdery crystals (Diethyl ether-methylene chloride-n-hexane) | 131–132 (decomposed) |
| 61 | 3-CH₃ | H | 5-F | H | 8 | Light brown powdery crystals (Methylene chloride-diethyl ether) | 112.5–114.5 (decomposed) |
| 62 | 3-CH₃ | 4-OCH₃ | 5-Cl | 6-Cl | 8 | Light brown powdery crystals (Methylene chloride-diethyle ether) | 138–139 (decomposed) |
| 63 | 3-CH₃ | 4-OCH₃ | 5-OC₂H₅ | 6-F | 8 | White powdery crystals (Methylene chloride-diethyl ether-n-hexane) | 129–130 (decomposed) |
| 64 | 3-CH₃ | 4-OCH₃ | 5-F | 6-F | 8 | White powdery crystals (Methylene chloride-diethyl ether) | 142.5–143.5 (decomposed) |

TABLE 4-continued

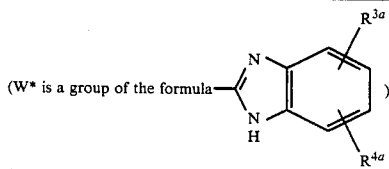

| Example No. | $R^{1a}$ | $R^{2a}$ | $R^{3a}$ | $R^{4a}$ | Substituted position of the formula —S—W* ↓ O | Crystal form (Recrystallization solvent) | Melting point (°C.) |
|---|---|---|---|---|---|---|---|
| 64a | 3-$CH_3$ | 4-$OCH_3$ | 5-F | 6-$OCH_3$ | 8 | White powdery crystals (Methylene cloride-diethyl ether-n-hexane) | 142–143 (decomposed) |
| 64b | 3-$CH_3$ | 4-$OCH_3$ | 5-$OCH_3$ | H | 8 | Light yellow powdery crystals (Methylene chloride-diethyl ether-n-hexane) | 125–127 (decomposed) |
| 64c | 3-$CH_3$ | 4-$OCH_3$ | 5-Cl | H | 8 | White powdery crystals (Methylene chloride-diethyl ether-n-hexane) | 104–105 (decomposed) |
| 64d | H | 4-$OCH_3$ | 5-F | H | 8 | White powdery crystals (Methylene chloride-diethyl ether) | 138–139 (decomposed) |
| 64e | 3-$CH_3$ | H | 5-Cl | 6-Cl | 8 | Light brown powdery crystals (Methylene chloride-diethyl ether-n-hexane) | 132–133 (decomposed) |
| 64f | 3-$CH_3$ | H | 5-$CH_3$ | 6-$CH_3$ | 8 | White powdery crystals (Methylene chloride-diethyl ether) | 134–135 (decomposed) |

(W* is a group of the formula—

(14) NMR (CDCl$_3$) δ: 1.70–2.10 (m, 2H), 2.10–2.60 (m, 2H), 2.70 (t, 2H), 4.90 (t, 1H), 6.90–7.70 (m, 4H), 7.83 (bs, 1H), 8.23 (dd, 1H).
(15) NMR (CDCl$_3$) δ: 1.70–2.20 (m, 2H), 2.20–2.50 (m, 2H), 2.20 (s, 3H), 2.70 (t, 2H), 4.83 (t, 1H), 2.70 (t, 2H), 4.83 (t, 1H), 7.10–7.50 (m, 2H), 7.20–7.80 (m, 2H), 8.18 (d, 1H).
(16) NMR (CDCl$_3$) δ: 1.70–2.60 (m, 4H), 2.20 (s, 3H), 2.47 (s, 3H), 2.70 (t, 2H), 4.80 (t, 1H), 7.20–7.30 (m, 2H), 7.40 (bs, 1H), 7.53 (d, 1H), 8.20 (d, 1H).
(17) NMR (CDCl$_3$) δ: 1.70–2.10 (m, 2H), 2.10–2.50 (m, 2H), 2.20 (s, 3H), 2.50–2.90 (m, 2H), 2.67 (s, 3H), 4.87 (t, 1H), 7.17 (bs, 1H), 7.63 (d, 1H), 7.97 (dd, 1H), 8.17 (d, 1H), 8.28 (d, 1H).
(18) NMR (CDCl$_3$) δ: 1.70–3.00 (m, 6H), 2.10 (s, 3H), 3.83 (s, 3H), 4.80 (t, 1H), 6.70–7.10 (m, 3H), 7.30–7.70 (m, 1H), 8.28 (d, 1H).
(19) NMR (CDCl$_3$) δ: 1.60–3.00 (m, 4H), 2.33 (s, 3H), 2.70 (t, 2H), 3.87 (s, 3H), 4.73 (t, 1H), 6.80–7.10 (m, 3H), 7.10–7.30 (m, 1H), 7.53 (dd, 1H).
(20) NMR (CDCl$_3$) δ: 1.50–3.00 (m, 6H), 3.84 (s, 3H), 3.87 (s, 3H), 4.78 (t, 1H), 6.60–6.80 (m, 1H), 6.90–7.20 (m, 2H), 7.40–7.80 (m, 1H), 8.41 (d, 1H).
(21) NMR (CDCl$_3$) δ: 1.60–2.60 (m, 4H), 2.12 (s, 3H), 2.67 (t, 2H), 4.87 (t, 1H), 7.00 (d, 1H), 7.50 (dd, 1H), 7.66 (d, 1H), 8.85 (bs, 1H), 8.04 (d, 1H).

EXAMPLE 65

2.80 Grams of sodium hydroxide was dissolved in 15 ml of water and 200 ml of methanol, then to this solution was added 10.63 g of 2-mercapto-5-methoxybenzimidazole and the reaction mixture was heated with stirring at 55° C. for 30 minutes. Next, 13.33 g of 3-methyl-8-bromo-5,6,7,8-tetrahydroquinoline was added to the reaction mixture, then the whole reaction mixture was stirred under heating for 2.5 hours. After the reaction was completed, the solvent was removed by evaporation under reduced pressure, then to the residued thus obtained was added a small amount of 30% sodium hydroxide aqueous solution, and extracted with chloroform. The chloroform layer was washed wih an aqueous solution saturated with sodium chloride, then the extract was dried with anhydrous magnesium sulfate, and the solvent was removed by evaporation under reduced pressure. The residue thus obtained was purified by means of a silica gel column chromatography (eluent: dichloromethane/methanol=100/1) to obtain 18.80 g of 3-methyl-8-(5-methoxy-2-benzimidazolyl)thio-5,6,7,8-tetrahydroquinoline as in the form of colorless caramel-like substance.

NMR (CDCl$_3$) δ: 1.60–2.00 (m, 2H), 2.00–2.40 (m, 2H), 2.27 (s, 3H), 2.72 (t, 2H), 3.78 (s, 3H), 4.78 (t, 1H), 6.77 (dd, 1H), 7.00 (d, 1H), 7.22 (d, 1H), 7.40 (d, 1H), 8.23 (d, 1H).

EXAMPLES 66-99

By procedures similar to those described in Example 65, by using suitable starting materials, there were prepared compounds of Examples 66-99 as shown in the following Table 5.

TABLE 5

| Example No. | $R^{1a}$ | $R^{2a}$ | $R^{3a}$ | $R^{4a}$ | Substituted position of the formula —S—W* | Crystal form (Recrystallization solvent) | Melting point (°C.) |
|---|---|---|---|---|---|---|---|
| 66 | H | H | 5-OCH$_3$ | H | 8 | Orange oily substance (24) | — |
| 67 | H | H | 5-CF$_3$ | H | 8 | Brown oily substance (25) | — |
| 68 | H | H | H | H | 8 | Colorless needle-like crystals (Acetonitrile) | 180–183 |
| 69 | H | H | 5-CH$_3$ | H | 8 | Colorless indefinite form crystals (26) | — |
| 70 | H | H | 5-Cl | H | 8 | Colorless oily substance (27) | — |
| 71 | H | H | 5-OCH$_3$ | 6-OCH$_3$ | 8 | Light yellow powdery crystals (Ethyl acetate) | 133–137 |
| 72 | 3-CH$_3$ | H | H | H | 8 | Colorless needle-like crystals (Acetonitrile) | 189–190 |
| 73 | 3-CH$_3$ | H | 5-CH$_3$ | H | 8 | Colorless indefinite form crystals (28) | — |
| 74 | 3-CH$_3$ | H | 5-COCH$_3$ | H | 8 | Orange oily substance (29) | — |
| 75 | 3-CH$_3$ | H | 5-OCH$_3$ | 6-OCH$_3$ | 8 | Light skin color needle-like crystals (Acetonitrile) | 177.5–179 |
| 76 | H | 4-CH$_3$ | 5-OCH$_3$ | H | 8 | Colorless caramel-like substance (30) | — |
| 77 | H | 2-CH$_3$ | 5-OCH$_3$ | H | 8 | Yellow oily substance (31) | — |
| 78 | H | 4-OCH$_3$ | 5-OCH$_3$ | H | 8 | Yellow oily substance (32) | — |
| 79 | H | 4-OCH$_3$ | 5-CF$_3$ | H | 8 | Light orange oily substance (33) | — |
| 80 | H | 2-Cl | 5-OCH$_3$ | H | 8 | White powdery crystals (Ethyl acetate-n-hexane) | 152–154 |
| 81 | 3-CH$_3$ | 2-Cl | 5-OCH$_3$ | H | 8 | Light brown indefinite form crystals (34) | — |
| 82 | 3-CH$_3$ | H | 5-CF$_3$ | H | 8 | Colorless caramel-like substance (35) | — |
| 83 | H | 2-OH | 5-OCH$_3$ | H | 8 | White powdery crystals (Ethanol) | 217–218 (decomposed) |
| 84 | H | H | 5-NO$_2$ | H | 8 | Yellow needle-like crystals (Ethyl acetate-n-hexane) | 150–152 |
| 85 | H | H | 5-CH$_3$ | 6-CH$_3$ | 8 | White powdery crystals (Ethyl acetate) | 200.5–201.5 |
| 86 | H | H | H | 4-CH$_3$ | 8 | Colorless oily substance (36) | — |
| 87 | H | H | 5-F | H | 8 | Light brown oily substance (37) | — |
| 88 | 3-CH$_3$ | H | 5-OCH$_3$ | H | 5 | Colorless oily substance (38) | — |
| 89 | 3-CH$_3$ | H | 5-CF$_3$ | H | 5 | Colorless indefinite form substance (39) | — |
| 90 | 3-CH$_3$ | 4-OCH$_3$ | 5-F | H | 8 | Light yellow oily substance (40) | — |
| 91 | 3-CH$_3$ | 4-OCH$_3$ | H | H | 8 | Light yellow oily substance (41) | — |

TABLE 5-continued

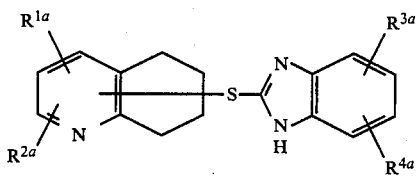

| Example No. | $R^{1a}$ | $R^{2a}$ | $R^{3a}$ | $R^{4a}$ | Substituted position of the formula —S—W* | Crystal form (Recrystallization solvent) | Melting point (°C.) |
|---|---|---|---|---|---|---|---|
| 92 | 3-$CH_3$ | 4-$OCH_3$ | 5-$CH_3$ | 6-$CH_3$ | 8 | White powdery crystals (Ethyl acetate-n-hexane) | 138–140 |
| 93 | H | H | 5-Cl | 6-Cl | 8 | Light brown prism-like crystals (Methylene chloride-diethyl ether) | 165–167 |
| 94 | H | H | 5-$OC_2H_5$ | 6-F | 8 | Light yellow oily substance (42) | — |
| 95 | H | H | 5-F | 6-F | 8 | Light yellow oily substance (43) | — |
| 96 | 3-$CH_3$ | H | 5-F | H | 8 | Colorless oily substance (44) | — |
| 97 | 3-$CH_3$ | 4-$OCH_3$ | 5-Cl | 6-Cl | 8 | Colorless oily substance (45) | — |
| 98 | 3-$CH_3$ | 4-$OCH_3$ | 5-$OC_2H_5$ | 6-F | 8 | Colorless oily substance (46) | — |
| 99 | 3-$CH_3$ | 4-$OCH_3$ | 5-F | 6-F | 8 | Colorless oily substance (47) | — |
| 99a | 3-$CH_3$ | 4-$OCH_3$ | 5-F | 6-$OCH_3$ | 8 | Light brown oily substance (47a) | — |
| 99b | 3-$CH_3$ | 4-$OCH_3$ | 5-$OCH_3$ | H | 8 | Light brown oily substance (47b) | — |
| 99c | 3-$CH_3$ | 4-$OCH_3$ | 5-Cl | H | 8 | Light brown oily substance (47c) | — |
| 99d | H | 4-$OCH_3$ | 5-F | H | 8 | Light brown oily substance (47d) | — |
| 99e | 3-$CH_3$ | H | 5-Cl | 6-Cl | 8 | Brown needle-like crystals (Ethyl acetate-n-hexane) | 163–165 (½ hydrate) |
| 99f | 3-$CH_3$ | H | 5-$CH_3$ | 6-$CH_3$ | 8 | Light brown oily substance (47e) | — |

TABLE 5-continued (Structure: a tetrahydroquinoline with substituents $R^{1a}$, $R^{2a}$ connected via a thiomethyl-type linkage through S to a benzimidazole bearing $R^{3a}$, $R^{4a}$, N-H)

| Example No. | $R^{1a}$ | $R^{2a}$ | $R^{3a}$ | $R^{4a}$ | Substituted position of the formula —S—W* | Crystal form (Recrystallization solvent) | Melting point (°C.) |
|---|---|---|---|---|---|---|---|

(W* is a group of the formula — [benzimidazolyl with $R^{3a}$, $R^{4a}$, N-H] )

(24) NMR (CDCl₃) δ: 1.50–2.10 (m, 2H), 2.10–2.50 (m, 2H), 2.50–3.00 (m, 2H), 3.80 (s, 3H), 4.90 (t, 1H), 6.70–7.60 (m, 5H), 8.33 (dd, 1H).
(25) NMR (CDCl₃) δ: 1.70–2.20 (m, 2H), 2.20–2.50 (m, 2H), 2.83 (t, 2H), 4.90 (t, 1H), 7.00–7.70 (m, 4H), 7.80 (bs, 1H), 8.47 (dd, 1H).
(26) NMR (CDCl₃) δ: 1.70–2.20 (m, 2H), 2.20–2.60 (m, 2H), 2.47 (s, 3H), 2.87 (t, 2H), 4.77 (6; 1H), 6.90–7.70 (m, 5H), 8.50 (dd, 1H).
(27) NMR (CDCl₃) δ: 1.70–2.10 (m, 2H), 2.20–2.50 (m, 2H), 2.86 (t, 2H), 4.80 (t, 1H), 7.00–7.70 (m, 5H), 8.44 (dd, 1H).
(28) NMR (CDCl₃) δ: 1.60–2.20 (m, 2H), 2.20–2.60 (m, 2H), 2.30 (s, 3H), 2.47 (s, 3H), 2.80 (t, 2H), 4.77 (t, 1H), 7.00 (dd, 1H), 7.30–7.60 (m, 3H), 8.30 (d, 1H).
(29) NMR (CDCl₃) δ: 1.60–2.20 (m, 2H), 2.20–2.60 (m, 2H), 2.37 (s, 3H), 2.67 (s, 3H), 2.87 (t, 2H), 4.83 (t, 1H), 7.37 (d, 1H), 7.57 (d, 1H), 7.90 (dd, 1H), 8.20 (d, 1H) 8.33 (d, 1H).
(30) NMR (CDCl₃) δ: 1.70–2.50 (m, 4H), 2.27 (s, 3H), 2.50–2.80 (m, 2H), 3.83 (s, 3H), 4.73 (t, 1H), 6.80 (dd, 1H), 6.90–7.10 (m, 2H), 7.40 (d, 1H), 8.33 (d, 1H).
(31) NMR (CDCl₃) δ: 1.70–2.10 (m, 2H), 2.10–2.40 (m, 2H), 2.57 (s, 3H), 2.73 (t, 2H), 3.82 (s, 3H), 4.70 (t, 1H), 6.70–7.10 (m, 3H), 7.20–7.50 (m, 2H).
(32) NMR (CDCl₃) δ: 1.60–2.20 (m, 2H), 2.20–2.50 (m, 2H), 2.50–3.10 (m, 2H), 3.83 (s, 3H), 3.90 (s, 3H), 4.70 (t, 1H), 6.50–6.90 (m, 2H), 7.03 (bs, 1H), 7.43 (d, 1H), 8.40 (d, 1H).
(33) NMR (CDCl₃) δ: 1.70–2.10 (m, 2H), 2.10–2.40 (m, 2H), 2.40–2.80 (m, 2H), 3.87 (s, 3H), 4.87 (t, 1H), 6.97 (d, 1H), 7.33 (dd, 1H), 7.53 (d, 1H), 7.77 (bs, 1H), 8.30 (d, 1H).
(34) NMR (CDCl₃) δ: 1.70–2.10 (m, 2H), 2.20–2.50 (m, 2H), 2.35 (s, 3H), 2.77 (t, 2H), 4.54 (t, 1H), 6.82 (dd, 1H), 7.05 (d, 1H), 7.33 (s, 1H), 7.46 (d, 1H).
(35) NMR (CDCl₃) δ: 1.70–2.10 (m, 2H), 2.10–2.50 (m, 2H), 2.27 (s, 3H), 2.73 (t, 2H), 4.93 (t, 1H), 7.20–7.60 (m, 3H), 7.77 (bs, 1H), 8.23 (d, 1H).
(36) NMR (CDCl₃) δ: 1.80–2.20 (m, 2H), 2.20–2.50 (m, 2H), 2.62 (s, 3H), 2.87 (t, 2H), 4.78 (t, 1H), 6.90–7.60 (m, 5H), 8.48 (dd, 1H).
(37) NMR (CDCl₃) δ: 1.70–2.10 (m, 2H), 2.20–2.50 (m, 2H), 2.85 (t, 2H), 4.82 (t, 1H), 6.75–7.55 (m, 5H), 8.47 (dd, 1H).
(38) NMR (CDCl₃) δ: 1.60–2.40 (m, 4H), 2.13 (s, 3H), 2.70–3.10 (m, 2H), 3.83 (s, 3H), 5.10–5.30 (m, 1H), 6.87 (dd, 2H), 7.10–7.50 (m, 2H), 8.20 (d, 1H), 12.00 (brod, 1H).
(39) NMR (CDCl₃) δ: 1.60–2.50 (m, 4H), 2.22 (s, 3H), 2.70–3.10 (m, 2H), 5.30–5.50 (m, 1H), 7.30–8.00 (m, 4H), 8.27 (d, 1H).
(40) NMR (CDCl₃) δ: 1.70–2.10 (m, 2H), 2.10–2.40 (m, 2H), 2.24 (s, 3H), 2.60–2.90 (m, 2H), 3.78 (s, 3H), 4.80 (t, 1H), 6.70–7.50 (m, 3H), 8.25 (s, 1H).
(41) NMR (CDCl₃) δ: 1.70–2.10 (m, 2H), 2.10–2.40 (m, 2H), 2.23 (s, 3H), 2.60–2.90 (m, 2H), 3.77 (s, 3H), 4.80 (t, 1H), 7.00–7.60 (m, 4H), 8.27 (s, 1H).
(42) NMR (CDCl₃) δ: 1.50 (t, 3H), 1.80–2.00 (m, 2H), 2.10–2.70 (m, 2H), 2.74 (t, 2H), 4.13 (q, 2H), 4.88 (t, 1H), 7.00–7.40 (m, 4H), 8.33 (dd, 1H).
(43) NMR (CDCl₃) δ: 1.70–2.10 (m, 2H), 2.10–2.50 (m, 2H), 2.82 (t, 2H), 4.92 (t, 1H), 7.00–7.50 (m, 4H), 8.42 (dd, 1H).
(44) NMR (CDCl₃) δ: 1.70–2.10 (m, 2H), 2.10–2.60 (m, 2H), 2.27 (s, 1H), 2.75 (t, 2H), 4.82 (t, 1H), 6.70–7.50 (m, 3H), 7.24 (d, 1H), 8.25 (d, 1H).
(45) NMR (CDCl₃) δ: 1.70–2.10 (m, 2H), 2.10–2.50 (m, 2H), 2.25 (s, 3H), 2.60–2.90 (m, 2H), 3.80 (s, 3H), 4.84 (t, 1H), 7.53 (s, 2H), 8.23 (s, 1H).
(46) NMR (CDCl₃) δ: 1.43 (t, 3H), 1.70–2.10 (m, 2H), 2.10–2.50 (m, 2H), 2.26 (s, 3H), 2.60–2.90 (m, 2H), 3.80 (s, 3H), 4.08 (q, 2H), 4.76 (t, 1H), 7.10 (d, 1H), 7.20 (d, 1H), 8.27 (s, 1H).
(47) NMR (CDCl₃) δ: 1.70–2.10 (m, 2H), 2.10–2.50 (m, 2H), 2.26 (s, 3H), 2.60–2.90 (m, 2H), 3.80 (s, 3H), 4.82 (t, 1H), 7.20 (d, 1H), 7.20 (d, 1H), 8.25 (s, 1H).
(47a) NMR (CDCl₃) δ: 1.70–2.10 (m, 2H), 2.27 (s, 3H), 2.10–2.50 (m, 2H), 2.60–2.90 (m, 2H), 3.80 (s, 3H), 3.88 (s, 3H), 4.78 (t, 1H), 7.13 (d, 1H), 7.26 (d, 1H), 8.28 (s, 1H).
(47b) NMR (CDCl₃) δ: 1.70–2.10 (m, 2H), 2.27 (s, 3H), 2.10–2.40 (m, 2H), 2.60–2.90 (m, 2H), 3.80 (s, 6H), 4.75 (t, 1H), 6.78 (dd, 1H), 7.02 (d, 1H), 7.42 (d, 1H), 8.28 (s, 1H).
(47c) NMR (CDCl₃) δ: 1.70–2.10 (m, 2H), 2.27 (s, 3H), 2.10–2.50 (m, 2H), 2.60–2.90 (m, 2H), 3.80 (s, 3H), 4.78 (t, 1H), 7.08 (dd, 1H), 7.42 (d, 1H), 7.48 (d, 1H), 8.27 (s, 1H).
(47d) NMR (CDCl₃) δ: 1.70–2.10 (m, 2H), 2.20–2.50 (m, 2H), 2.50–3.00 (m, 2H), 3.90 (s, 3H), 4.72 (t, 1H), 6.72 (d, 1H), 6.70–7.60 (m, 3H), 8.39 (d, 1H).
(47e) NMR (CDCl₃) δ: 1.70–2.10 (m, 2H), 2.27 (s, 3H), 2.32 (s, 6H), 2.10–2.40 (m, 2H), 2.73 (t, 2H), 4.76 (t, 1H), 7.20 (d, 1H), 7.30 (s, 2H), 8.26 (d, 1H).

EXAMPLE 100

0.55 Gram of 2-chloro-5-methoxybenzimidazole, 0.2 g of thiourea and 10 ml of ethanol were mixed together and refluxed for 2 hours. Then, 5 ml of an aqueous solution containing 0.5 g of 3-methyl-8-bromo-5,6,7,8-tetrahydroquinoline and 0.3 g of sodium hydroxide was added thereto, and the resulting mixture was refluxed for 5 hours. After the reaction was completed, ethanol was removed by evaporation, to the residue thus obtained was added water, then extracted with chloroform, the chloroform extract was dried with anhydrous magnesium sulfate, and chloroform was removed by evaporation. The residue thus obtained was purified by means of a silica gel column chromatography (eluent: dichloromethane/methanol=100/1) to yield 0.5 g of 8-(5-methoxy-2-benzimidazolyl)thio-3-methyl-5,6,7,8-tetrahydroquinoline in the form of colorless caramel-like substance.

NMR (CDCl₃) δ: 1.60–2.00 (m, 2H), 2.00–2.40 (m, 2H), 2.27 (s, 3H), 2.72 (t, 2H), 3.78 (s, 3H), 4.78 (t, 1H), 6.77 (dd, 1H), 7.00 (d, 1H), 7.22 (d, 1H), 7.40 (d, 1H), 8.23 (d, 1H).

By a procedure similar to that described in Example 100, by using suitable starting materials, there were prepared compounds of Examples 66–99.

EXAMPLE 101

20 Milliliters of 20% hydrochloric acid was added to 0.8 g of 2-chloro-8-[(5-methoxy-2-benzimidazolyl)thio]-5,6,7,8-tetraydroquinoline, and the mixture was stirred at 70° to 80° C. for 1 hour. After cooling the reaction mixture, the crystals precipitated in the reaction mixture were collected by filtration, and recrystallized from ethanol to obtain 0.4 g of 2-hydroxy-8-[(5-methoxy-2-benzimidazolyl)thio]-5,6,7,8-tetrahydroquinoline in the form of white powdery crystals. Melting point: 217°–218° C. (decomposed.

EXAMPLE 102

1.5 Grams of 2-mercaptoimidazo[4,5-b]pyridine was dissolved in 50 ml of dimethylformamide, to this solution was added, under ice-cooled condition, 0.88 g of 60% sodium hydride (in oil), and the mixture was stirred at the same temperature for 30 minutes. Then, to this reaction mixture was added 2.2 g of 2-chloromethyl-3,5-dimethyl-4-methoxypyridine hydrochloride and the whole mixture was heated at 70° to 80° C. under stirring condition for 3 hours. After the reaction was completed, dimethylformamide was removed by evaporation, and to the residue thus obtained was added water, and then extracted with chloroform. The chloroform extract was washed with water, and dried with anhydrous magnesium sulfate. Chloroform was removed by evaporation, then the residue thus obtained was recrystallized from ethanol to obtain 1.3 g of 2-[(3,5-dimethyl-4-methoxy-2-pyridyl)methylthio]imidazo[4,5-b]pyridine in the form of white powdery crystals. Melting point: 186°–188° C.

EXAMPLES 103–116

By a method similar to that described in Example 102, by using suitable starting materials, there were prepared compounds of Examples 103–116 represented by the general formula (20) wherein $l=0$ as shown in Table 6 as follows.

TABLE 6

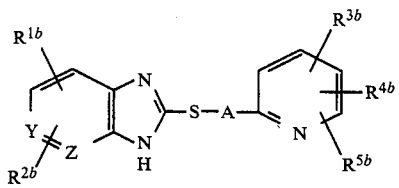

| Example No. | $R^{1b}$ | $R^{2b}$ | $R^{3b}$ | $R^{4b}$ | $R^{5b}$ | Z | Y | A | Crystal form (Recrystallization solvent) | Melting point (°C.) |
|---|---|---|---|---|---|---|---|---|---|---|
| 103 | H | H | H | 4-OCH$_3$ | H | N | CH | CH$_2$ | White granular crystals (Ethyl acetate) | 111–113 |
| 104 | H | H | 3-CH$_3$ | 4-OCH$_3$ | 5-CH$_3$ | N | CH | CH$_2$ | White powdery crystals (Ethanol) | 186–188 |
| 105 | H | 5-COOCH$_3$ | 3-CH$_3$ | 4-OCH$_3$ | 5-CH$_3$ | N | CH | CH$_2$ | Yellow granular crystals (Ethanol) | 177–179 |
| 106 | H | 5-Cl | 3-CH$_3$ | 4-OCH$_3$ | 5-CH$_3$ | N | CH | CH$_2$ | Yellow powdery crystals (Ethanol-ethyl acetate) | 221–222 |
| 107 | H | 5-CH$_3$ | 3-CH$_3$ | 4-OCH$_3$ | 5-CH$_3$ | N | CH | CH$_2$ | Yellow powdery crystals (Ethanol) | 188.5–190 |
| 108 | 6-NH$_2$ | H | 3-CH$_3$ | 4-OCH$_3$ | 5-CH$_3$ | N | CH | CH$_2$ | Yellow granular crystals (Ethanol) | 208–209 |
| 109 | 4-CH$_3$ | 5-Br | 3-CH$_3$ | 4-OCH$_3$ | 5-CH$_3$ | N | CH | CH$_2$ | Yellow powdery crystals (Ethanol) | 223–224 |
| 110 | 6-OH | H | 3-CH$_3$ | 4-OCH$_3$ | 5-CH$_3$ | N | CH | CH$_2$ | Yellow powdery crystals (Ethanol) | 178–179.5 |
| 111 | H | 5-NH$_2$ | 3-CH$_3$ | 4-OCH$_3$ | 5-CH$_3$ | N | CH | CH$_2$ | Red powdery crystals (Ethanol-dichloromethane) | 210–211 |
| 112 | H | H | H | H | H | CH | N | CH$_2$ | Colorless needle-like crystals (Ethyl acetate) | 130–131 |
| 113 | H | H | H | 4-OCH$_3$ | H | CH | N | CH$_2$ | White granular crystals (Ethyl acetate) | 111–113 |
| 114 | H | H | 3-CH$_3$ | 4-OCH$_3$ | 5-CH$_3$ | CH | N | CH$_2$ | White powdery crystals (Ethyl acetate-diethyl ether) | 164–166 |
| 115 | H | 5-COOCH$_3$ | H | 4-OCH$_3$ | H | N | CH | CH$_2$ | NMR (48) | — |

TABLE 6-continued

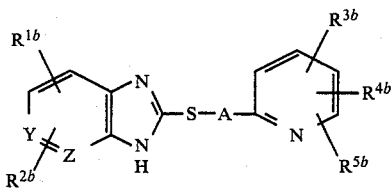

| Example No. | $R^{1b}$ | $R^{2b}$ | $R^{3b}$ | $R^{4b}$ | $R^{5b}$ | Z | Y | A | Crystal form (Recrystallization solvent) | Melting point (°C.) |
|---|---|---|---|---|---|---|---|---|---|---|
| 116 | H | H | H | H | H | N | CH | $CH_2CH_2$ | NMR (49) | — |

(48) NMR —6) δ: 3.80 (3H, s), 3.87 (3H, s), 4.67 (2H, s), 6.87 (1H, dd), 7.15 (1H, d), 8.25 (1H, d), 8.34 (1H, d), 8.82 (1H, d).
(49) NMR —6) δ: 3.25 (2H, t), 3.72 (2H, t), 7.00–7.40 (3H, m), 7.60–8.00 (2H, m), 8.53 (1H, dd).

EXAMPLE 117

0.4 Gram of 2-[(3,5-dimethyl-4-methoxy-2-pyridyl)-methylthio]imidazo[4,5-b]pyridine was dissolved in 40 ml of chloroform, then this solution was stirred under ice-cooling condition, 0.27 g of m-chloroperbenzoic acid (85%) was added thereto. The whole reaction mixture was stirred at the same temperature for 20 minutes. After the reaction was completed, the reaction mixture was concentrated under reduced pressure, the residue thus obtained was washed with diethyl ether. Recrystallization from ethanol to yield 1.15 g of 2-[(3,5-dimethyl-4-methoxy-2-pyridyl)methylsulfinyl-]imidazo[4,5-b]pyridine in the form of light brown powdery crystals. Melting point: 169°–170° C.

EXAMPLES 118–128

By a method similar to that described in Example 117, by using suitable starting materials, there were prepared compounds of Examples 118–128 represented by the general formula (20) wherein l=1 as shown in Table 7 as follows.

TABLE 7

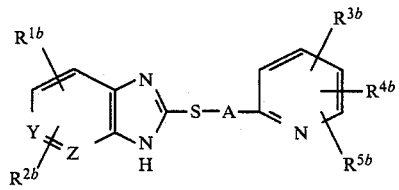

| Example No. | $R^{1b}$ | $R^{2b}$ | $R^{3b}$ | $R^{4b}$ | $R^{5b}$ | Z | Y | A | Crystal form (Recrystallization solvent) | Melting point (°C.) |
|---|---|---|---|---|---|---|---|---|---|---|
| 118 | H | H | H | H | H | N | CH | $CH_2$ | White powdery crystals (Ethanol) | 164–165 (decomposed) |
| 119 | H | H | H | 4-$OCH_3$ | H | N | CH | $CH_2$ | Brown powdery crystals (Ethanol) | 135–136 (decomposed) |
| 120 | H | H | 3-$CH_3$ | 4-$OCH_3$ | 5-$CH_3$ | N | CH | $CH_2$ | White needle-like crystals (Dimethylformamide-diethyl ether) | 167–170 (decomposed) |
| 121 | H | 5-C(=O)—$OCH_3$ | 3-$CH_3$ | 4-$OCH_3$ | 5-$CH_3$ | N | CH | $CH_2$ | Yellow powdery crystals (Dimethylformamide-diethyl ether) | 141–142 (decomposed) |
| 122 | H | 5-Cl | 3-$CH_3$ | 4-$OCH_3$ | 5-$CH_3$ | N | CH | $CH_2$ | White powdery crystals (Dimethylformamide-diethyl ether) | 139–140 (decomposed) |
| 123 | H | 5-$CH_3$ | 3-$CH_3$ | 4-$OCH_3$ | 5-$CH_3$ | N | CH | $CH_2$ | White powdery crystals (Dimethylformamide-diethyl ether) | 164–165 (decomposed) |
| 124 | 6-$NH_2$ | H | 3-$CH_3$ | 4-$OCH_3$ | 5-$CH_3$ | N | CH | $CH_2$ | Yellow powdery crystals (Dimethylformamide-diethyl ether) | 173–175 (decomposed) |
| 125 | 4-$CH_3$ | 5-Br | 3-$CH_3$ | 4-$OCH_3$ | 5-$CH_3$ | N | CH | $CH_2$ | White powdery crystals (Dimethylformamide-diethyl ether) | 115–117 (decomposed) |
| 126 | H | H | H | H | H | CH | N | $CH_2$ | Yellow powdery crystals (Ethanol) | 177–178 (decomposed) |
| 127 | H | H | H | 4-$OCH_3$ | H | CH | N | $CH_2$ | Brown powdery | 135–136 |

TABLE 7-continued

[Structure: imidazo[4,5-b] ring with R1b, R2b substituents, Y, Z positions, linked via S-A to a pyridine ring with R3b, R4b, R5b substituents]

| Example No. | R1b | R2b | R3b | R4b | R5b | Z | Y | A | Crystal form (Recrystallization solvent) | Melting point (°C.) |
|---|---|---|---|---|---|---|---|---|---|---|
| 128 | H | H | 3-CH$_3$ | 4-OCH$_3$ | 5-CH$_3$ | CH | N | CH$_2$ | crystals (Ethanol) Red-brown powdery crystals (Ethanol-chloroform) | (decomposed) 188–189 |

EXAMPLE 129

737 Milligrams of 2-chloro-imidazo[4,5-b]pyridine, 0.4 g of thiourea and 20 ml of ethanol were mixed together and this mixture was refluxed for 2 hours. Next, 666 mg of 2-chloromethyl-3,5-dimethyl-4-methoxypyridine hydrochloride was added to the reaction mixture and refluxed for 5 hours. After the reaction was completed, ethanol was removed by evaporation, then to the residue thus obtained was added water and this solution was extracted with chloroform. The chloroform extract was dried with anhydrous magnesium sulfate and chloroform was removed by evaporation. The residue thus obtained was recrystallized from ethanol to obtain 450 mg of 2-[(3,5-dimethyl-4-methoxy-2-pyridyl)methylthio]imidazo[4,5-b]pyridine in the form of white powdery crystals. Melting point: 186°–188° C.

By a method similar to that described in Example 129, and by using suitable starting materials, there were prepared compounds of Examples 103–115.

EXAMPLE 130

0.2 Gram of 6-amino-2-[(3,5-dimethyl-4-methoxy-2-pyridyl)methylthio]imidazo[4,5-b]pyridine was dissolved in a mixture consisting of 3 ml of water and 0.1 ml of concentrated sulfuric acid. This mixture was stirred at 0° C., and 59 mg of sodium nitrite was added, then the mixture was further stirred at the same temperature for 1 hour. The reaction solution was neutralized by adding 4N-sodium hydroxide aqueous solution, and the crystals formed were collected by filtration. Recrystallized from ethanol to obtain 0.2 g of 6-hydroxy-2-[(3,5-dimethyl-4-methoxy-2-pyridyl)methylthio]imidazo[4,5-b]pyridine in the form of yellow powdery crystals. Melting point: 178°–179.5° C.

Pharmacological activities of compounds of the present invention are shown in the following test results.

PHARMACOLOGICAL TEST-1

Inhibitory effect test for the activity of H$^+$-K$^+$-ATPase

Test method

H$^+$-K$^+$-ATPase (hydrogen-potassium-activated adenosine triphosphatase) (protein content: 10 mcg) which was prepared from the stomach of swine was added to PIPES-tris buffer[PIPES-tris(hydroxymethyl)-2-amino-1,3-propanediol buffer (pH=6.1) containing 2 mM of piperazine-N,N'-bis(2-ethanesulfonic acid)], then the resulting mixture was let allowed to stand at room temperature.

Each of the test compounds was dissolved in dimethylformamide, and the dimethylformamide solution was added to the above-mentioned H$^+$-K$^+$-ATPase buffer solution so as to adjust the final concentration of the test compound to 1.0%. Each of thus prepared mixture was reacted at room temperature for 30 minutes.

Next, the above-mentioned reaction mixture was divided into two portions, and to the one portion thereof was added 1 ml of 75 mM PIPES-tris buffer solution (pH=7.4) (containing 4 mM of MgCl$_2$, 4 mM of Na$_2$ATP and 20 mM of KCl), on the other hand, to another portion of the reaction mixture was added 1 ml of 75 mM PIPES-tris buffer solution (pH=7.4) (containing 4 mM of MgCl$_2$ and 4 mM of Na$_2$ATP), respectively. Each of these two series of sample solutions was separately reacted at 37° C. for 30 minutes. Then to each of these reaction mixtures was added 0.3 ml of 40% trichloroacetic acid to terminate the reaction, and was subjected to centrifugal separation at 3,000 rpm for 10 minutes to obtain the supernatant. Next, the inorganic phosphoric acid formed in the reaction mixture was determined by a method according to the article by C. H. Fiske and Y. Subbarow: J. Biol. Chem., Vol. 66, pages 375–400, (1925). The difference of the value obtained by substracting the quantity of inorganic phosphoric acid determined by using PIPES-tris buffer solution without containing 20 mM of KCl from the quantity of inorganic phosphoric acid determined by using PIPES-tris buffer solution containing 20 mM of KCl, was converted into as activity value of enzyme with respect to the unit protein and unit time.

Inhibitory rate (%) of each of the test compounds was obtained from the activity value of the enzyme at the respective dosages in the test groups and those of obtained from the control group, then IC$_{50}$ (50% inhibition dosage of each of the test compounds) was calculated from the inhibitory rate (%). The results are shown in Table 8 as follows.

(2) Test compounds (1) 4-Allyloxy-8-(2-benzimidazolyl)sulfinyl-3-methyl-5,6,7,8-tetrahydroquinoline
(2) 4-Allyloxy-8-(5,6-difluoro-2-benzimidazolyl)sulfinyl-3-methyl-5,6,7,8-tetrahydroquinoline
(3) 8-(5-Fluoro-2-benzimidazolyl)sulfinyl-3-methyl-4-propargyloxy-5,6,7,8-tetrahydroquinoline (4) 4-Allyloxy-8-(5,6-dimethyl-2-benzimidazolyl)sulfinyl-3-methyl-5,6,7,8-tetrahydroquinoline
(5) 4-Allyloxy-8-(5,6-dichloro-2-benzimidazolyl)sulfinyl-3-methyl-5,6,7,8-tetrahydroquinoline
(6) 8-(5,6-Dimethyl-2-benzimidazolyl)sulfinyl-3-methyl-4-propargyloxy-5,6,7,8-tetrahydroquinoline
(7) 8-(2-Benzimidazolyl)sulfinyl-3-methyl-4-propargyloxy-5,6,7,8-tetrahydroquinoline
(8) 8-(5,6-Dichloro-2-benzimidazolyl)sulfinyl-3-methyl-4-propargyloxy-5,6,7,8-tetrahydroquinoline
(9) 8-(2-Benzimidazolyl)sulfinyl-4-(2-methoxyethoxy)-3-methyl-5,6,7,8-tetrahydroquinoline
(10) 8-(5-Fluoro-2-benzimidazolyl)sulfinyl-4-(2-methoxyethoxy)-3-methyl-5,6,7,8-tetrahydroquinoline
(11) 4-Allyloxy-8-(5-fluoro-2-benzimidazolyl)sulfinyl-3-methyl-5,6,7,8-tetrahydroquinoline
(12) 8-(2-Benzimidazolyl)sulfinyl-5,6,7,8-tetrahydroquinoline
(13) 4-Methyl-8-(5-methoxy-2-benzimidazolyl)sulfinyl-5,6,7,8-tetrahydroquinoline
(14) 2-Methyl-8-(5-methoxy-2-benzimidazolyl)sulfinyl-5,6,7,8-tetrahydroquinoline
(15) 3-Methyl-8-(2-benzimidazolyl)sulfinyl-5,6,7,8-tetrahydroquinoline
(16) 3-Methyl-8-(5-methyl-2-benzimidazolyl)sulfinyl-5,6,7,8-tetrahydroquinoline
(17) 8-(5-Methyl-2-benzimidazolyl)sulfinyl-5,6,7,8-tetrahydroquinoline
(18) 3-Methyl-8-(5-acetyl-2-benzimidazolyl)sulfinyl-5,6,7,8-tetrahydroquinoline
(19) 3-Methyl-8-(5,6-dimethoxy-2-benzimidazolyl)sulfinyl-5,6,7,8-tetrahydroquinoline
(20) 8-(5-Chloro-2-benzimidazolyl)sulfinyl-5,6,7,8-tetrahydroquinoline
(21) 2-Chloro-8-(5-methoxy-2-benzimidazolyl)sulfinyl-5,6,7,8-tetrahydroquinoline
(22) 2-Chloro-3-methyl-8-(5-methoxy-2-benzimidazolyl)sulfinyl-5,6,7,8-tetrahydroquinoline
(23) 8-(5-Methoxy-2-benzimidazolyl)sulfinyl-5,6,7,8-tetrahydroquinoline
(24) 4-Methoxy-8-(5-methoxy-2-benzimidazolyl)sulfinyl-5,6,7,8-tetrahydroquinoline
(25) 4-Methoxy-8-(5-trifluoromethyl-2-benzimidazolyl)sulfinyl-5,6,7,8-tetrahydroquinoline
(26) 3-Methyl-8-(5-methoxy-2-benzimidazolyl)sulfinyl-5,6,7,8-tetrahydroquinoline
(27) 3-Methyl-8-(5-trifluoromethyl-2-benzimidazolyl)sulfinyl-5,6,7,8-tetrahydroquinoline
(28) 8-(5-Trifluoromethyl-2-benzimidazolyl)sulfinyl-5,6,7,8-tetrahydroquinoline
(29) 2-Hydroxy-8-(5-methoxy-2-benzimidazolyl)sulfinyl-5,6,7,8-tetrahydroquinoline
(30) 8-(5,6-Dimethoxy-2-benzimidazolyl)sulfinyl-5,6,7,8-tetrahydroquinoline
(31) 8-(5-Nitro-2-benzimidazolyl)sulfinyl-5,6,7,8-tetrahydroquinoline
(32) 8-(5-Fluoro-2-benzimidazolyl)sulfinyl-5,6,7,8-tetrahydroquinoline
(33) 8-(4-Methyl-2-benzimidazolyl)sulfinyl-5,6,7,8-tetrahydroquinoline
(34) 3-Methyl-4-methoxy-8-(5-fluoro-2-benzimidazolyl)sulfinyl-5,6,7,8-tetrahydroquinoline
(35) 3-Methyl-4-methoxy-8-(2-benzimidazolyl)sulfinyl-5,6,7,8-tetrahydroquinoline
(36) 8-(5,6-Dichloro-2-benzimidazolyl)sulfinyl-5,6,7,8-tetrahydroquinoline
(37) 8-(5-Ethoxy-6-fluoro-2-benzimidazolyl)sulfinyl-5,6,7,8-tetrahydroquinoline
(38) 3-Methyl-4-methoxy-8-(5,6-dimethyl-2-benzimidazolyl)sulfinyl-5,6,7,8-tetrahydroquinoline
(39) 3-Methyl-5-(5-trifluoromethyl-2-benzimidazolyl)sulfinyl-5,6,7,8-tetrahydroquinoline
(40) 3-Methyl-8-(5-fluoro-2-benzimidazolyl)sulfinyl-5,6,7,8-tetrahydroquinoline
(41) 3-Methyl-4-methoxy-8-(5,6-dichloro-2-benzimidazolyl)sulfinyl-5,6,7,8-tetrahydroquinoline
(42) 3-Methyl-4-methoxy-8-(5-ethoxy-6-fluoro-2-benzimidazolyl)sulfinyl-5,6,7,8-tetrahydroquinoline
(43) 3-Methyl-4-methoxy-8-(5,6-difluoro-2-benzimidazolyl)sulfinyl-5,6,7,8-tetrahydroquinoline
(44) 3-Methyl-5-(5-trifluoromethyl-2-benzimidazolyl)sulfinyl-5,6,7,8-tetrahydroquinoline
(45) 5-Bromo-2-[(3,5-dimethyl-4-methoxy-2-pyridyl)methylsulfinyl]imidazo[4,5-b]pyridine
(46) 2-[(3,5-Dimethyl-4-methoxy-2-pyridyl)methylsulfinyl]imidazo[4,5-c]pyridine
(47) 2-(2-Pyridylmethylthio)imidazo[4,5-b]pyridine (A compound being disclosed in British Pat. No. 1,234,058)
(48) 3-Methyl-4-methoxy-8-(5-fluoro-6-methoxy-2-benzimidazolyl)sulfinyl-5,6,7,8-tetrahydroquinoline
(49) 3-Methyl-4-methoxy-8-(5-methoxy-2-benzimidazolyl)sulfinyl-5,6,7,8-tetrahydroquinoline
(50) 3-Methyl-4-methoxy-8-(5-chloro-2-benzimidazolyl)sulfinyl-5,6,7,8-tetrahydroquinoline
(51) 4-Methoxy-8-(5-fluoro-2-benzimidazolyl)sulfinyl-5,6,7,8-tetrahydroquinoline
(52) 3-Methyl-8-(5,6-dichloro-2-benzimidazolyl)sulfinyl-5,6,7,8-tetrahydroquinoline
(53) 3-Methyl-8-(5,6-dimethyl-2-benzimidazolyl)sulfinyl-5,6,7,8-tetrahydroquinoline (3) Test results The test results are shown in the following Table 8.

TABLE 8

| Test compound No. | $IC_{50}$ (M) | Test compound No. | $IC_{50}$ (M) |
| --- | --- | --- | --- |
| 1 | $7.4 \times 10^{-7}$ | 25 | $2.9 \times 10^{-6}$ |
| 2 | $1.8 \times 10^{-6}$ | 26 | $3.7 \times 10^{-6}$ |
| 3 | $1.1 \times 10^{-6}$ | 27 | $1.5 \times 10^{-6}$ |
| 4 | $6.1 \times 10^{-7}$ | 28 | $1.9 \times 10^{-6}$ |
| 5 | $3.1 \times 10^{-7}$ | 29 | $2.3 \times 10^{-6}$ |
| 6 | $4.6 \times 10^{-7}$ | 30 | $9.3 \times 10^{-7}$ |
| 7 | $1.2 \times 10^{-6}$ | 31 | $2.9 \times 10^{-6}$ |
| 8 | $2.9 \times 10^{-7}$ | 32 | $1.7 \times 10^{-6}$ |
| 9 | $8.4 \times 10^{-7}$ | 33 | $2.6 \times 10^{-6}$ |
| 10 | $8.7 \times 10^{-7}$ | 34 | $2.2 \times 10^{-7}$ |
| 11 | $7.3 \times 10^{-7}$ | 35 | $2.5 \times 10^{-7}$ |
| 12 | $1.2 \times 10^{-6}$ | 36 | $7.0 \times 10^{-7}$ |
| 13 | $1.1 \times 10^{-6}$ | 37 | $3.4 \times 10^{-6}$ |
| 14 | $1.5 \times 10^{-6}$ | 38 | $3.4 \times 10^{-7}$ |
| 15 | $1.8 \times 10^{-6}$ | 39 | $2.98 \times 10^{-6}$ |
| 16 | $1.1 \times 10^{-6}$ | 40 | $1.9 \times 10^{-6}$ |
| 17 | $1.9 \times 10^{-6}$ | 41 | $9.9 \times 10^{-8}$ |
| 18 | $3.2 \times 10^{-6}$ | 42 | $2.4 \times 10^{-7}$ |
| 19 | $3.1 \times 10^{-6}$ | 43 | $2.8 \times 10^{-7}$ |
| 20 | $1.0 \times 10^{-6}$ | 44 | $2.9 \times 10^{-6}$ |
| 21 | $2.7 \times 10^{-6}$ | 45 | $2.34 \times 10^{-6}$ |
| 22 | $2.1 \times 10^{-6}$ | 46 | $2.92 \times 10^{-5}$ |
| 23 | $1.9 \times 10^{-6}$ | 47 | Over $1.0 \times 10^{-4}$ |
| 24 | $7.6 \times 10^{-6}$ | | |
| 48 | $3.1 \times 10^{-7}$ | 51 | $9.9 \times 10^{-8}$ |
| 49 | $2.8 \times 10^{-7}$ | 52 | $2.3 \times 10^{-7}$ |
| 50 | $1.8 \times 10^{-7}$ | 53 | $5.8 \times 10^{-7}$ |

PHARMACOLOGICAL TEST-2

Inhibitory effect test for the secretion of hydrochloric acid in the stomach

(1) Test method

Wistar strain male rats were used as test animals. The test animals were abstained from food for 24 hours, then the pyloric sphincter of the test animal was ligated under anesthetized condition with urethane (1.5 g/kg), and a perfusion cannula for the stomach was inserted into the stomach.

The stomach was perfused with physiological saline through a peroral catheter, and the quantity of gastric juice secreted was measured by determining the pH and by titrating the total acidity of the perfusate.

The secretion of gastric juice was accelerated by injecting histamine dihydrochloride as the secretion stimulant in the rate of 1 mg/kg/hour continuously through the femoral vein, then the effect of each of the compounds was tested. Each of the test compounds was dissolved in dimethylformamide, and the predetermined dosage (maximum: 30 mg/kg) of each of the test compounds was administered by injecting the test compound solution into the duodenum.

Inhibition rate (%) of the secretion of hydrochloric acid was calculated by taking the value of the hydrochloric acid secreted before the administration of each of the test compounds as the reference.

$ED_{50}$ value of each of the test compounds was calculated from the inhibitory rate (%) of each of the test compounds and treated mathematically by probit (probability unit) analysis.

(2) Test results

The test results are shown in the following Table 9.

TABLE 9

| Test compound No. | $ED_{50}$ (mg/kg) |
|---|---|
| 12 | 8.5 |
| 17 | 17.2 |
| 20 | 4.4 |
| 26 | 15.7 |
| 32 | 5.2 |

What is claimed is:

1. Imidazopyridine compounds and salts thereof represented by the formula

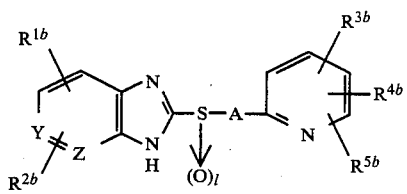

wherein any one of Z and Y is a group of the formula —CH= and the other one is a nitrogen atom —N=; $R^{1b}$ and $R^{2b}$ are the same or different from each other, and are each a hydrogen atom, $C_1$–$C_6$ alkoxy-carbonyl group, a halogen atom, $C_1$–$C_6$ alkyl group, an amino group or a hydroxy group; $R^{3b}$, $R^{4b}$ and $R^{5b}$ are the same or different from each other, and are each a hydrogen atom, $C_1$–$C_6$ alkoxy group or $C_1$–$C_6$ alkyl group; A is $C_1$–$C_6$ alkylene group; l is 0 to 1; provided that when Y is a group of the formula —CH=, Z is a nitrogen atom —N=, and l is 0, then $R^{3b}$, $R^{4b}$ and $R^{5b}$ should not all be hydrogen atoms.

2. The imidazopyridine compounds according to claim 1, wherein l is 0.

3. The imidazopyridine compounds according to claim 1, wherein l is 1.

4. The imidazopyridine compounds according to claim 3, wherein Z is a nitrogen atom —N= and Y is a group of the formula —CH=.

5. The imidazopyridine compounds according to claim 3, wherein Z is a group of the formula —CH= and Y is a nitrogen atom —N=.

6. The imidazopyridine compounds according to claim 4 or 5, wherein $R^{1b}$ and $R^{2b}$ are the same or different from each other, and are each a hydrogen atom, $C_1$–$C_6$ alkyl group or a halogen atom.

7. The imidazopyridine compounds according to claim 4 or 5, wherein $R^{1b}$ and $R^{2b}$ are the same or different from each other, and are each $C_1$–$C_6$ alkoxycarbonyl group, an amino group or a hydroxy group.

8. The imidazopyridine compounds according to claim 6 or 7, wherein $R^{3b}$, $R^{4b}$ and $R^{5b}$ are the same or different, and are each $C_1$–$C_6$ alkoxy group or $C_1$–$C_6$ alkyl group.

9. The imidazopyridine derivatives according to claim 8, wherein A is methylene group.

10. 5-Methyl-2-[(3,5-dimethyl-4-methoxy-2-pyridyl)methylsulfinyl]imidazo[4,5-b]pyridine.

11. 5-Chloro-2-[(3,5-dimethyl-4-methoxy-2-pyridyl)methylsulfinyl]imidazo[4,5-b]pyridine.

12. 2-[(3,5-Dimethyl-4-methoxy-2-pyridyl)methylsulfinyl]imidazo[4,5-b]pyridine.

13. An anti-peptic ulcer composition containing, as an active ingredient, an imidazopyridine compound of claim 1.

* * * * *

UNITED STATES PATENT AND TRADEMARK OFFICE
CERTIFICATE OF CORRECTION

PATENT NO. : 4,880,815
DATED : November 14, 1989
INVENTOR(S) : Minoru Uchida et al.

It is certified that error appears in the above-identified patent and that said Letters Patent is hereby corrected as shown below:

Claim 1, column 52, line 19, "1" (first occurrence) should be --$\ell$--.

Claim 1, column 52, line 21, "1" should be --$\ell$--;

Claim 2, column 52, line 24, "1" (second occurrence) should be --$\ell$--;

and

Claim 3, column 52, line 26, "1" (second occurrence) should be --$\ell$--.

Signed and Sealed this

Sixth Day of August, 1991

*Attest:*

*Attesting Officer*

HARRY F. MANBECK, JR.

*Commissioner of Patents and Trademarks*